United States Patent
Tverskoy

(10) Patent No.: US 8,852,152 B2
(45) Date of Patent: Oct. 7, 2014

(54) INFUSION PUMP SYSTEMS AND METHODS

(75) Inventor: Boris Tverskoy, Palo Alto, CA (US)

(73) Assignee: Asante Solutions, Inc., Sunnyvale, CA (US)

(*) Notice: Subject to any disclaimer, the term of this patent is extended or adjusted under 35 U.S.C. 154(b) by 776 days.

(21) Appl. No.: 13/023,820

(22) Filed: Feb. 9, 2011

(65) Prior Publication Data

US 2012/0203178 A1 Aug. 9, 2012

(51) Int. Cl.
- A61M 1/00 (2006.01)
- A61M 5/142 (2006.01)
- H02J 7/00 (2006.01)
- H01H 47/00 (2006.01)
- H02J 9/00 (2006.01)

(52) U.S. Cl.
CPC ... *A61M 5/14244* (2013.01); *A61M 2205/3569* (2013.01); *A61M 2205/3576* (2013.01)
USPC ............ 604/151; 307/150; 307/130; 320/135

(58) Field of Classification Search
CPC .............. A61M 2205/8206; A61M 2205/8212
USPC ........................................................ 604/151
See application file for complete search history.

(56) References Cited

U.S. PATENT DOCUMENTS

| | | |
|---|---|---|
| 2,605,765 A | 8/1952 | Kollsman |
| 3,886,938 A | 6/1975 | Szabo et al. |
| 4,077,405 A | 3/1978 | Haerten et al. |
| 4,231,368 A | 11/1980 | Becker |
| 4,265,241 A | 5/1981 | Portner et al. |
| 4,300,554 A | 11/1981 | Hessberg et al. |
| 4,313,439 A | 2/1982 | Babb et al. |
| 4,398,908 A | 8/1983 | Siposs |
| 4,435,173 A | 3/1984 | Siposs et al. |
| 4,443,218 A | 4/1984 | DeCant, Jr. et al. |
| 4,493,704 A | 1/1985 | Beard et al. |
| 4,529,401 A | 7/1985 | Leslie et al. |
| 4,850,817 A | 7/1989 | Nason et al. |
| 5,045,064 A | 9/1991 | Idriss |
| 5,088,981 A | 2/1992 | Howson et al. |
| 5,190,522 A | 3/1993 | Wojcicki et al. |
| 5,250,027 A | 10/1993 | Lewis et al. |
| 5,261,882 A | 11/1993 | Sealfon et al. |

(Continued)

FOREIGN PATENT DOCUMENTS

| | | |
|---|---|---|
| CA | 2543545 | 5/2005 |
| DE | 196 27 619 A | 1/1998 |

(Continued)

OTHER PUBLICATIONS

Seiko Instruments, Inc., Datasheet "S-8211C Series Battery Protection IC for 1-Cell Pack," Rev.6.0_00, (2010).

(Continued)

*Primary Examiner* — Quynh-Nhu H Vu
*Assistant Examiner* — Jenna Zhang
(74) *Attorney, Agent, or Firm* — Fish & Richardson P.C.

(57) ABSTRACT

Some embodiments of an infusion pump system can include a controller in electrical communication with a pump device so as to provide selected dosages of a medicine to a user over a period of time. The infusion pump system can employ a number of power management techniques to reduce the likelihood current drain of a rechargeable battery of the infusion pump system.

20 Claims, 9 Drawing Sheets

(56) References Cited

U.S. PATENT DOCUMENTS

| | | |
|---|---|---|
| 5,314,412 A | 5/1994 | Rex |
| 5,335,994 A | 8/1994 | Weynant Nee Girones |
| 5,338,157 A | 8/1994 | Blomquist |
| 5,342,180 A | 8/1994 | Daoud |
| 5,395,340 A | 3/1995 | Lee |
| 5,411,487 A | 5/1995 | Castagna |
| 5,545,143 A | 8/1996 | Fischell et al. |
| 5,551,850 A | 9/1996 | Williamson et al. |
| 5,558,639 A | 9/1996 | Gangemi et al. |
| 5,569,186 A | 10/1996 | Lord et al. |
| 5,626,566 A | 5/1997 | Petersen et al. |
| 5,637,095 A | 6/1997 | Nason et al. |
| 5,665,065 A | 9/1997 | Colman et al. |
| 5,712,795 A | 1/1998 | Layman et al. |
| 5,717,308 A | 2/1998 | Nishitani et al. |
| 5,741,216 A | 4/1998 | Hemmingsen et al. |
| 5,772,635 A | 6/1998 | Dastur et al. |
| 5,816,306 A | 10/1998 | Giacomel |
| 5,852,803 A | 12/1998 | Ashby, III et al. |
| 5,919,167 A | 7/1999 | Mulhauser |
| 5,925,018 A | 7/1999 | Ungerstedt |
| 5,928,201 A | 7/1999 | Poulsen et al. |
| 5,947,934 A | 9/1999 | Hansen et al. |
| 5,951,530 A | 9/1999 | Steengaard et al. |
| 5,957,889 A | 9/1999 | Poulsen et al. |
| 5,984,894 A | 11/1999 | Poulsen et al. |
| 5,984,897 A | 11/1999 | Petersen et al. |
| 5,997,475 A | 12/1999 | Bortz |
| 6,003,736 A | 12/1999 | Ljunggren |
| 6,010,485 A | 1/2000 | Buch-Rasmussen et al. |
| 6,033,377 A | 3/2000 | Rasmussen et al. |
| 6,045,537 A | 4/2000 | Klitmose |
| 6,074,372 A | 6/2000 | Hansen |
| 6,110,149 A | 8/2000 | Klitgaard et al. |
| 6,144,186 A | 11/2000 | Thandiwe et al. |
| 6,156,014 A | 12/2000 | Petersen et al. |
| 6,171,276 B1 | 1/2001 | Lippe et al. |
| 6,231,540 B1 | 5/2001 | Smedegaard |
| 6,248,067 B1 | 6/2001 | Causey, III et al. |
| 6,248,090 B1 | 6/2001 | Jensen et al. |
| 6,248,093 B1 | 6/2001 | Moberg |
| 6,277,098 B1 | 8/2001 | Klitmose et al. |
| 6,302,855 B1 | 10/2001 | Lav et al. |
| 6,302,869 B1 | 10/2001 | Klitgaard |
| 6,375,638 B2 | 4/2002 | Nason et al. |
| 6,379,339 B1 | 4/2002 | Klitgaard et al. |
| 6,381,496 B1 | 4/2002 | Meadows et al. |
| 6,404,098 B1 | 6/2002 | Kayama et al. |
| 6,427,088 B1 | 7/2002 | Bowman, IV et al. |
| 6,461,331 B1 | 10/2002 | Van Antwerp |
| 6,474,219 B2 | 11/2002 | Klitmose et al. |
| 6,485,461 B1 | 11/2002 | Mason et al. |
| 6,508,788 B2 | 1/2003 | Preuthun |
| 6,524,280 B2 | 2/2003 | Hansen et al. |
| 6,533,183 B2 | 3/2003 | Aasmul et al. |
| 6,537,251 B2 | 3/2003 | Klitmose |
| 6,540,672 B1 | 4/2003 | Simonsen et al. |
| 6,544,229 B1 | 4/2003 | Danby et al. |
| 6,547,764 B2 | 4/2003 | Larsen et al. |
| 6,551,276 B1 | 4/2003 | Mann et al. |
| 6,554,798 B1 | 4/2003 | Mann et al. |
| 6,554,800 B1 | 4/2003 | Nezhadian et al. |
| 6,558,320 B1 | 5/2003 | Causey, III et al. |
| 6,558,351 B1 | 5/2003 | Steil et al. |
| 6,562,001 B2 | 5/2003 | Lebel et al. |
| 6,562,011 B1 | 5/2003 | Buch-Rasmussen et al. |
| 6,564,105 B2 | 5/2003 | Starkweather et al. |
| 6,569,126 B1 | 5/2003 | Poulsen et al. |
| 6,571,128 B2 | 5/2003 | Lebel et al. |
| 6,577,899 B2 | 6/2003 | Lebel et al. |
| 6,582,404 B1 | 6/2003 | Klitgaard et al. |
| 6,585,644 B2 | 7/2003 | Lebel et al. |
| 6,585,699 B2 | 7/2003 | Ljunggren et al. |
| 6,595,756 B2 | 7/2003 | Gray et al. |
| 6,605,067 B1 | 8/2003 | Larsen |
| 6,613,019 B2 | 9/2003 | Munk |
| 6,641,533 B2 | 11/2003 | Causey, III et al. |
| 6,648,821 B2 | 11/2003 | Lebel et al. |
| 6,650,951 B1 | 11/2003 | Jones et al. |
| 6,656,158 B2 | 12/2003 | Mahoney et al. |
| 6,656,159 B2 | 12/2003 | Flaherty |
| 6,659,948 B2 | 12/2003 | Lebel et al. |
| 6,659,978 B1 | 12/2003 | Kasuga et al. |
| 6,659,980 B2 | 12/2003 | Moberg et al. |
| 6,663,602 B2 | 12/2003 | Møller |
| 6,668,196 B1 | 12/2003 | Villegas et al. |
| 6,669,669 B2 | 12/2003 | Flaherty et al. |
| 6,687,546 B2 | 2/2004 | Lebel et al. |
| 6,691,043 B2 | 2/2004 | Ribeiro, Jr. |
| 6,692,457 B2 | 2/2004 | Flaherty |
| 6,692,472 B2 | 2/2004 | Hansen et al. |
| 6,694,191 B2 | 2/2004 | Starkweather et al. |
| 6,699,218 B2 | 3/2004 | Flaherty et al. |
| 6,702,779 B2 | 3/2004 | Connelly et al. |
| 6,715,516 B2 | 4/2004 | Ohms et al. |
| 6,716,198 B2 | 4/2004 | Larsen |
| 6,723,072 B2 | 4/2004 | Flaherty et al. |
| 6,733,446 B2 | 5/2004 | Lebel et al. |
| 6,736,796 B2 | 5/2004 | Shekalim |
| 6,740,059 B2 | 5/2004 | Flaherty |
| 6,740,072 B2 | 5/2004 | Starkweather et al. |
| 6,740,075 B2 | 5/2004 | Lebel et al. |
| 6,744,350 B2 | 6/2004 | Blomquist |
| 6,749,587 B2 | 6/2004 | Flaherty |
| 6,752,787 B1 | 6/2004 | Causey, III et al. |
| 6,758,810 B2 | 7/2004 | Lebel et al. |
| 6,768,425 B2 | 7/2004 | Flaherty et al. |
| 6,780,156 B2 | 8/2004 | Haueter et al. |
| 6,786,246 B2 | 9/2004 | Ohms et al. |
| 6,786,890 B2 | 9/2004 | Preuthun et al. |
| 6,796,970 B1 | 9/2004 | Klitmose et al. |
| 6,799,149 B2 | 9/2004 | Hartlaub |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,827,702 B2 | 12/2004 | Lebel et al. |
| 6,830,558 B2 | 12/2004 | Flaherty et al. |
| 6,852,104 B2 | 2/2005 | Blomquist |
| 6,854,620 B2 | 2/2005 | Ramey |
| 6,854,653 B2 | 2/2005 | Eilersen |
| 6,855,129 B2 | 2/2005 | Jensen et al. |
| 6,872,200 B2 | 3/2005 | Mann et al. |
| 6,873,268 B2 | 3/2005 | Lebel et al. |
| 6,878,132 B2 | 4/2005 | Kipfer |
| 6,893,415 B2 | 5/2005 | Madsen et al. |
| 6,899,695 B2 | 5/2005 | Herrera |
| 6,899,699 B2 | 5/2005 | Enggaard |
| 6,922,590 B1 | 7/2005 | Whitehurst |
| 6,936,006 B2 | 8/2005 | Sabra |
| 6,936,029 B2 | 8/2005 | Mann et al. |
| 6,945,961 B2 | 9/2005 | Miller et al. |
| 6,948,918 B2 | 9/2005 | Hansen |
| 6,950,708 B2 | 9/2005 | Bowman, IV et al. |
| 6,958,705 B2 | 10/2005 | Lebel et al. |
| 6,960,192 B1 | 11/2005 | Flaherty et al. |
| 6,979,326 B2 | 12/2005 | Mann et al. |
| 6,997,911 B2 | 2/2006 | Klitmose |
| 6,997,920 B2 | 2/2006 | Mann et al. |
| 7,005,078 B2 | 2/2006 | Van Lintel et al. |
| 7,008,399 B2 | 3/2006 | Larsen et al. |
| 7,014,625 B2 | 3/2006 | Bengtsson |
| 7,018,360 B2 | 3/2006 | Flaherty et al. |
| 7,025,743 B2 | 4/2006 | Mann |
| 7,029,455 B2 | 4/2006 | Flaherty |
| 7,054,836 B2 | 5/2006 | Christensen et al. |
| 7,104,972 B2 | 9/2006 | Møller et al. |
| 7,128,727 B2 | 10/2006 | Flaherty et al. |
| 7,133,329 B2 | 11/2006 | Skyggebjerg et al. |
| 7,232,423 B2 | 6/2007 | Mernoe et al. |
| 7,404,796 B2 | 7/2008 | Ginsberg |
| 7,935,105 B2 | 5/2011 | Miller et al. |
| 8,105,279 B2 | 1/2012 | Mernoe et al. |

(56) References Cited

U.S. PATENT DOCUMENTS

| | | |
|---|---|---|
| 8,287,514 B2 | 10/2012 | Miller et al. |
| 2001/0056262 A1 | 12/2001 | Cabiri |
| 2002/0004651 A1 | 1/2002 | Ljndggreen et al. |
| 2002/0007154 A1 | 1/2002 | Hansen et al. |
| 2002/0040208 A1 | 4/2002 | Flaherty et al. |
| 2002/0091358 A1 | 7/2002 | Klitmose |
| 2002/0126036 A1 | 9/2002 | Flaherty et al. |
| 2003/0055380 A1 | 3/2003 | Flaherty |
| 2003/0065308 A1 | 4/2003 | Lebel et al. |
| 2003/0088238 A1 | 5/2003 | Poulsen |
| 2003/0199825 A1 | 10/2003 | Flaherty |
| 2003/0216683 A1 | 11/2003 | Shekalim |
| 2004/0008117 A1 | 1/2004 | Kawakami |
| 2004/0010207 A1 | 1/2004 | Flaherty et al. |
| 2004/0019325 A1 | 1/2004 | Shekalim |
| 2004/0064088 A1 | 4/2004 | Gorman et al. |
| 2004/0064096 A1 | 4/2004 | Flaherty et al. |
| 2004/0078028 A1 | 4/2004 | Flaherty et al. |
| 2004/0087894 A1 | 5/2004 | Flaherty |
| 2004/0092865 A1 | 5/2004 | Flaherty et al. |
| 2004/0092878 A1 | 5/2004 | Flaherty |
| 2004/0116866 A1 | 6/2004 | Gorman et al. |
| 2004/0127844 A1 | 7/2004 | Flaherty |
| 2004/0153032 A1 | 8/2004 | Garribotto et al. |
| 2004/0171983 A1 | 9/2004 | Sparks et al. |
| 2004/0176727 A1 | 9/2004 | Shekalim |
| 2004/0204673 A1 | 10/2004 | Flaherty |
| 2004/0220551 A1 | 11/2004 | Flaherty et al. |
| 2004/0235446 A1 | 11/2004 | Flaherty et al. |
| 2004/0260233 A1 | 12/2004 | Garibotto et al. |
| 2005/0021005 A1 | 1/2005 | Flaherty et al. |
| 2005/0022274 A1 | 1/2005 | Campbell et al. |
| 2005/0065760 A1 | 3/2005 | Murtfeldt et al. |
| 2005/0086410 A1 | 4/2005 | Landron et al. |
| 2005/0090808 A1 | 4/2005 | Malave et al. |
| 2005/0095063 A1 | 5/2005 | Fathallah |
| 2005/0160858 A1 | 7/2005 | Mernoe |
| 2005/0171512 A1 | 8/2005 | Flaherty |
| 2005/0182366 A1 | 8/2005 | Vogt et al. |
| 2005/0192561 A1 | 9/2005 | Mernoe |
| 2005/0203461 A1 | 9/2005 | Flaherty et al. |
| 2005/0215982 A1 | 9/2005 | Malave et al. |
| 2005/0222645 A1 | 10/2005 | Malave et al. |
| 2005/0238507 A1 | 10/2005 | DiIanni et al. |
| 2005/0245878 A1 | 11/2005 | Mernoe et al. |
| 2005/0251097 A1 | 11/2005 | Mernoe |
| 2005/0267402 A1 | 12/2005 | Stewart et al. |
| 2005/0273059 A1 | 12/2005 | Mernoe et al. |
| 2006/0041229 A1 | 2/2006 | Garibotto et al. |
| 2006/0047367 A1 | 3/2006 | Rogers et al. |
| 2006/0069382 A1 | 3/2006 | Pedersen |
| 2006/0074381 A1 | 4/2006 | Malave et al. |
| 2006/0079765 A1 | 4/2006 | Neer et al. |
| 2006/0095014 A1 | 5/2006 | Ethelfeld |
| 2006/0135913 A1 | 6/2006 | Ethelfeld |
| 2006/0142698 A1 | 6/2006 | Ethelfeld |
| 2006/0178633 A1 | 8/2006 | Garibotto et al. |
| 2006/0184119 A1 | 8/2006 | Remde et al. |
| 2006/0200073 A1 | 9/2006 | Radmer et al. |
| 2006/0206054 A1 | 9/2006 | Shekalim |
| 2006/0247581 A1 | 11/2006 | Pedersen et al. |
| 2007/0073228 A1 | 3/2007 | Mernoe et al. |
| 2007/0073235 A1 | 3/2007 | Estes et al. |
| 2007/0073236 A1 | 3/2007 | Mernoe et al. |
| 2007/0124002 A1 | 5/2007 | Estes et al. |
| 2007/0156092 A1 | 7/2007 | Estes et al. |
| 2007/0167905 A1 | 7/2007 | Estes et al. |
| 2007/0167912 A1 | 7/2007 | Causey et al. |
| 2007/0179444 A1 | 8/2007 | Causey et al. |
| 2008/0208627 A1 | 8/2008 | Skyggebjerg |
| 2008/0243079 A1* | 10/2008 | Wooley et al. ............... 604/154 |
| 2009/0069749 A1 | 3/2009 | Miller et al. |
| 2009/0295228 A1* | 12/2009 | Ochi ............................ 307/66 |
| 2011/0112504 A1 | 5/2011 | Causey et al. |
| 2012/0022496 A1 | 1/2012 | Causey et al. |
| 2012/0123384 A1 | 5/2012 | Mernoe et al. |
| 2012/0130312 A1 | 5/2012 | Mernoe et al. |
| 2012/0302991 A1 | 11/2012 | Blomquist et al. |
| 2013/0012917 A1 | 1/2013 | Miller et al. |

FOREIGN PATENT DOCUMENTS

| | | |
|---|---|---|
| DE | 102 36 669 | 2/2004 |
| EP | 0275213 | 3/1992 |
| EP | 0 496 141 | 7/1992 |
| EP | 0 612 004 | 8/1994 |
| EP | 1 045 146 | 10/2000 |
| EP | 1 136 698 | 9/2001 |
| EP | 1 177 802 | 2/2002 |
| EP | 0 721 358 | 5/2002 |
| EP | 1 384 490 | 1/2004 |
| EP | 1 495 775 | 1/2005 |
| EP | 1 527 792 | 5/2005 |
| EP | 1 754 498 | 2/2007 |
| FR | 2 585 252 | 1/1987 |
| GB | 747 701 | 4/1956 |
| GB | 2 218 831 | 11/1989 |
| WO | WO 90/15928 | 12/1990 |
| WO | WO 92/18175 | 10/1992 |
| WO | WO 97/21457 | 6/1997 |
| WO | WO 98/11927 | 3/1998 |
| WO | WO 98/57683 | 12/1998 |
| WO | WO 99/21596 | 5/1999 |
| WO | WO 99/39118 | 8/1999 |
| WO | WO 99/48546 | 9/1999 |
| WO | WO01/23277 | 4/2001 |
| WO | WO 01/72360 | 10/2001 |
| WO | WO 01/91822 | 12/2001 |
| WO | WO 01/91833 | 12/2001 |
| WO | WO 02/40083 | 5/2002 |
| WO | WO 02/057627 | 7/2002 |
| WO | WO 02/100469 | 12/2002 |
| WO | WO 03/103763 | 12/2003 |
| WO | WO 2004/056412 | 7/2004 |
| WO | WO 2004/110526 | 12/2004 |
| WO | WO 2005/002652 | 1/2005 |
| WO | WO 2005/039673 | 5/2005 |
| WO | WO 2005/072794 | 8/2005 |
| WO | WO 2005/072795 | 8/2005 |
| WO | WO 2006/105792 | 10/2006 |
| WO | WO 2006/105793 | 10/2006 |
| WO | WO 2006/105794 | 10/2006 |
| WO | WO2007/145951 | 12/2007 |

OTHER PUBLICATIONS

Medtronic News Release, "Medtronic Receives FDA Approval for World's First Insulin Pump with Real-time Continuous Glucose Monitoring," Apr. 13, 2006, 3 pages.

Debiotech News Release, "Debiotech reveals its new miniaturized Disposable Insulin Nanopump™ for Diabetes therapy," available at http://www.debiotech.com/news/nw_159.html Apr. 24, 2006, 3 pages.

Patent Abstracts of Japan, vol. 1999, No. 04, and JP 11 010036, Apr. 30, 1999 and Jan. 19, 1999, Toray Ind. Inc.

* cited by examiner

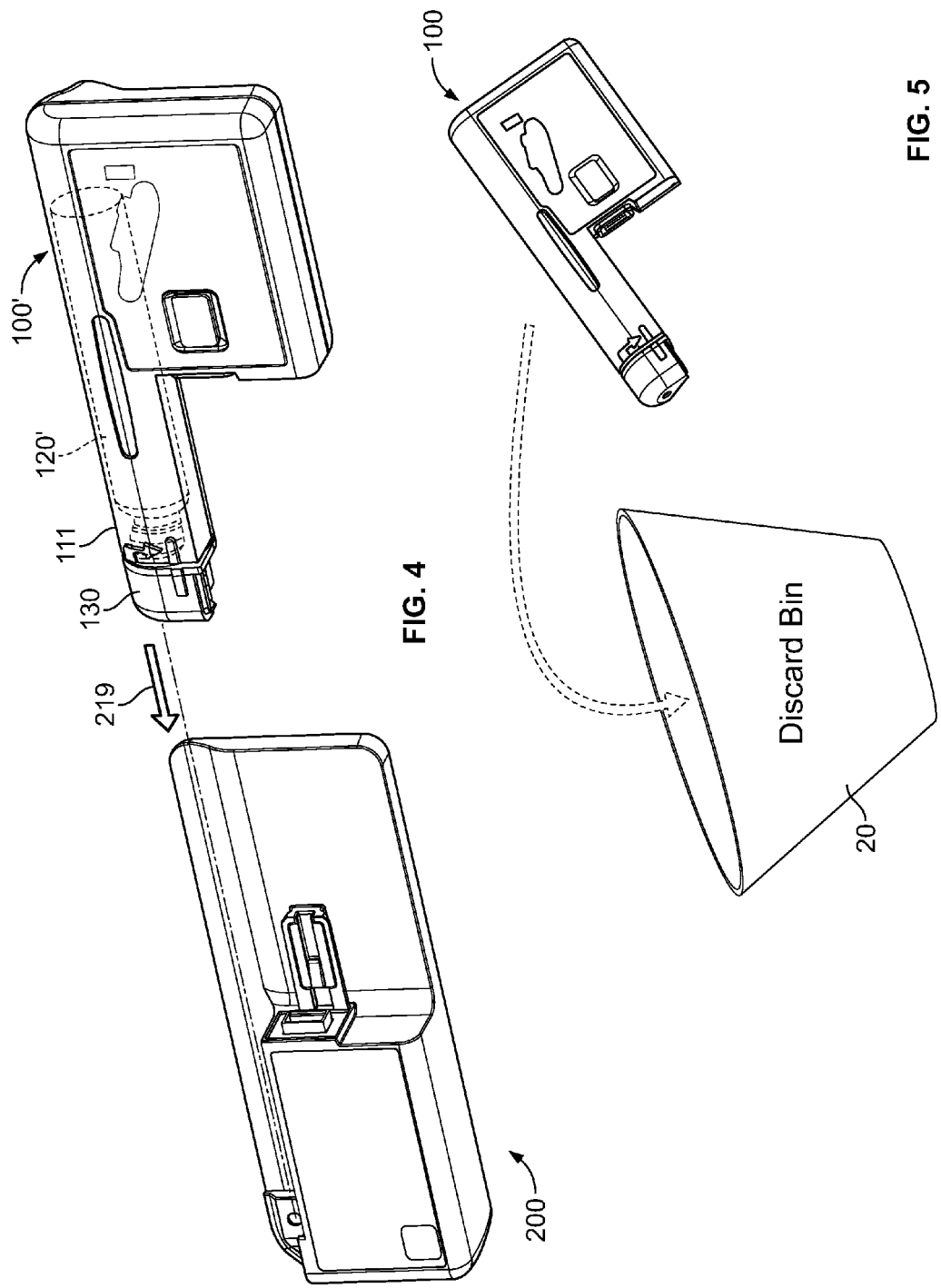

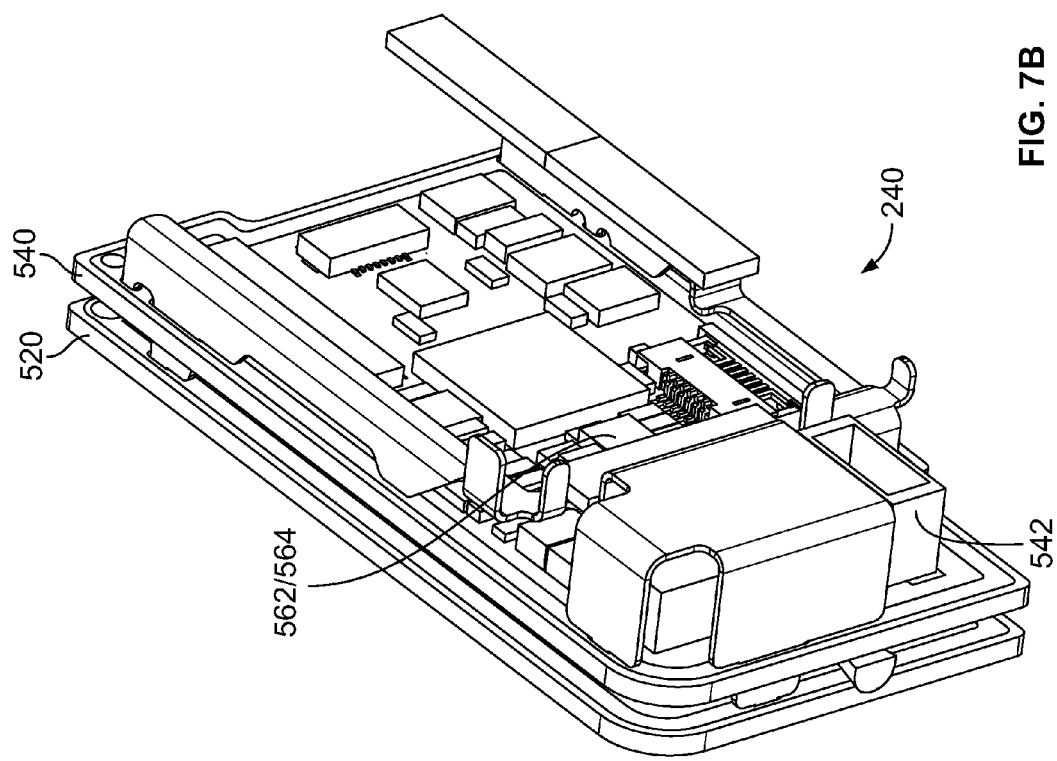
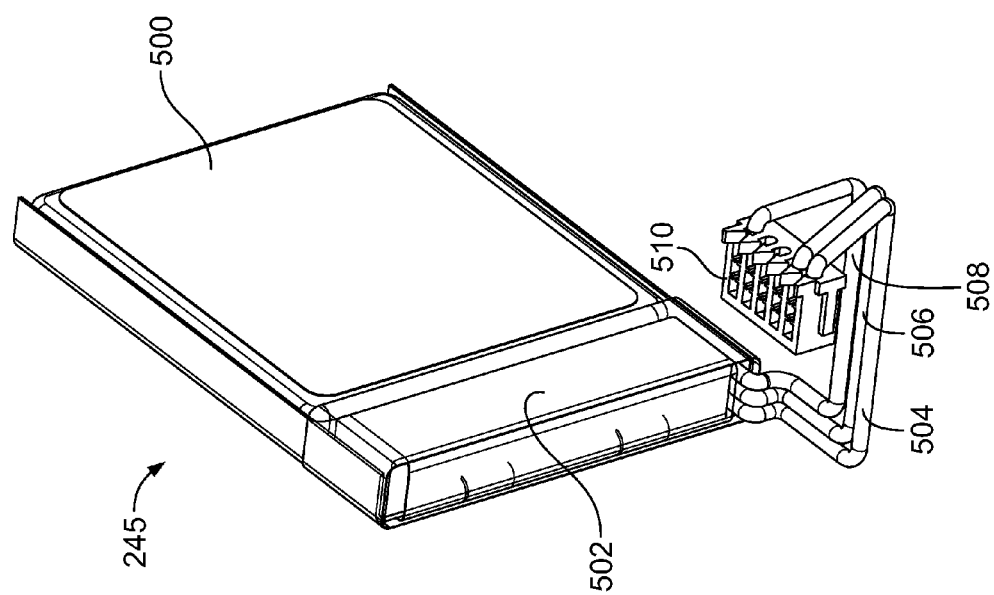
FIG. 7B

INFUSION PUMP SYSTEMS AND METHODS

TECHNICAL FIELD

This document relates to a portable infusion pump system, such as a wearable insulin pump system that delivers insulin to a user.

BACKGROUND

Pump devices are commonly used to deliver one or more fluids to a targeted individual. For example, a medical infusion pump device may be used to deliver a medicine to a patient as part of a medical treatment. The medicine that is delivered by the infusion pump device can depend on the condition of the patient and the desired treatment plan. For example, infusion pump devices have been used to deliver insulin to the vasculature of diabetes patients so as to regulate blood-glucose levels.

In some circumstances, the infusion pump devices may operate on battery power to facilitate portability of the pump devices. In some applications, it can be cost effective over the life of the infusion pump to utilize a rechargeable battery rather than a single use battery, as the rechargeable battery may be recharged many times, which can offset the higher initial cost of the rechargeable battery as compared to a single-use battery. Even during periods when the infusion pump device is not being used, circuitry of the device may drain current from the rechargeable battery. To reduce likelihood of an over-discharge condition of the rechargeable battery, which may damage the rechargeable battery and adversely affect its life cycle capacity, it is desirable to minimize idle current of the rechargeable battery during periods of non-use.

SUMMARY

Some embodiments of an infusion pump system can include a controller in electrical communication with a pump device so as to provide selected dosages of a medicine to a user over a period of time. The infusion pump system can employ a number of power management techniques to reduce the likelihood current drain of a rechargeable battery of the infusion pump system. Thus, the infusion pump system can preserve the energy supply of the rechargeable battery in an efficient manner to reduce the likelihood of over-discharge of the rechargeable battery, for example, during periods when the system is idle or stored prior to use (e.g., shelf life). In some circumstances, the infusion pump system can be configured in a manner that prolongs the useful life of the rechargeable battery.

In particular embodiments, a portable infusion pump system may include a pump device and a controller device that is electrically connectable to the pump device. The pump device may include a pump housing that defines a space to receive a medicine, and a drive system to dispense the medicine from the pump device when the medicine is received in the space of the pump housing. The controller device may electrically connect to the pump device so as to control dispensation of the medicine from the pump device. The controller device may include a battery pack including a voltage output terminal, a return terminal, a third terminal, and at least one rechargeable battery cell that is coupled to the voltage output terminal. The rechargeable battery cell may provide electrical energy to at least one of a component of the controller device and the drive system of the pump device. The controller device may further include a monitor circuit that senses a voltage of the at least one rechargeable battery cell, a first resistor coupled between the at least one rechargeable battery cell and a voltage sense terminal of the monitor circuit, and a second resistor coupled between the voltage sense terminal of the monitor circuit and the third terminal of the battery pack. When a low-resistance connection is provided between the third terminal of the battery pack and the return terminal of the battery pack, the monitor circuit can shift the battery pack to a low power mode that reduces electrical current drawn from the at least one rechargeable battery cell.

In other embodiments, a method of controlling a portable infusion pump system may include providing a controller device that is electrically connectable to a pump device so as to control dispensation of medicine from the pump device. The controller device may include a battery pack including a voltage output terminal, a return terminal, a third terminal, and at least one rechargeable battery cell that is coupled to the voltage output terminal. The rechargeable battery cell can be configured to provide electrical energy to at least one of a user interface component of the controller device and a drive system of the pump device. The controller device may further include a monitor circuit that senses a voltage of the at least one rechargeable battery cell, a first resistor coupled between the at least one rechargeable battery cell and a voltage sense terminal of the monitor circuit, and a second resistor coupled between the voltage sense terminal of the monitor circuit and the third terminal of the battery pack. The method may also include providing a low-resistance connection between the third terminal of the battery pack and the return terminal of the battery pack to cause the safety integrated circuit to put the battery pack in a low power mode that reduces electrical current drawn from the at least one rechargeable battery cell.

Some or all of the embodiments described herein may provide one or more of the following advantages. First, some embodiments of the infusion pump system may include a configuration minimizes an idle current drain of a rechargeable battery. This may preserve the energy supply of the rechargeable battery in an efficient manner to prevent over-discharge of the rechargeable battery and prolong the useful life of the rechargeable battery.

Second, certain embodiments of an infusion pump system may include a configuration that can place the rechargeable battery into a low power mode even when the rechargeable battery retains a substantially full charge level, which is greater than a predefined low voltage threshold value established by a battery monitoring circuit device. This may preserve the energy supply of the rechargeable battery in an efficient manner to prevent over-discharge of the rechargeable battery and prolong the useful life of the rechargeable battery.

Third, some embodiments of the infusion pump system can cause the rechargeable battery to enter a low power mode without an application of an external voltage source. This may provide convenience because the low power mode may be entered without having to connect a separate device or power source, thereby simplifying the manufacturing and storage process for the controller device.

Fourth, using techniques discussed herein, some embodiments can permit the rechargeable battery to be placed in the low power mode following manufacture of the rechargeable battery, or alternatively during assembly and production of the infusion pump system. This may preserve the energy supply of the rechargeable battery in an efficient manner to prevent over-discharge of the rechargeable battery, and may permit the rechargeable battery to retain charge so that the system is usable immediately upon unpacking after shipping and storage (e.g., a period of shelf life) of the system.

Fifth, some embodiments of the infusion pump system can cause the rechargeable battery to enter a low power mode following a user-initiated action, such as disconnecting the pump assembly from the controller device. This may preserve the energy supply of the rechargeable battery in an efficient manner to prevent over-discharge of the rechargeable battery and prolong the useful life of the rechargeable battery.

The details of one or more embodiments are set forth in the accompanying drawings and the description below. Other features, objects, and advantages will be apparent from the description and drawings, and from the claims.

DESCRIPTION OF DRAWINGS

FIGS. 4-5 are perspective views of the pump device of FIGS. 1-2 being discarded and the controller device of FIGS. 1-2 being reused with a new pump device.

FIGS. 7A and 7B are exploded perspective views of a portion of the controller device of FIG. 6.

DETAILED DESCRIPTION OF ILLUSTRATIVE EMBODIMENTS

Figure 1:
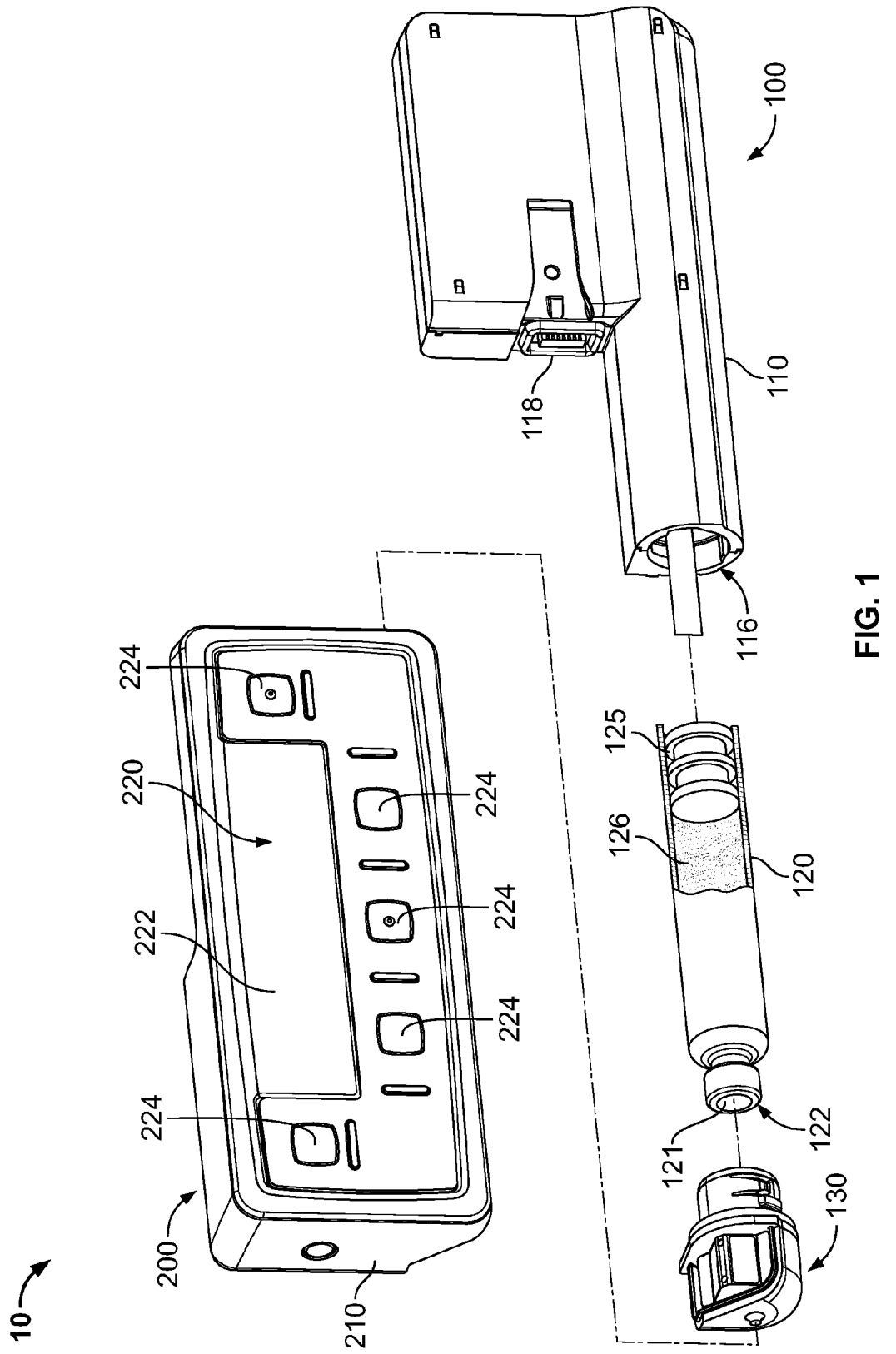
FIG. 1 is a perspective view of an infusion pump system in accordance with some embodiments.

Referring to FIG. 1, an infusion pump system 10 can include a pump device 100 and a controller device 200 that communicates with the pump device 100. The pump device 100 in this embodiment includes a housing structure 110 that defines a cavity 116 in which a fluid cartridge 120 can be received. The pump device 100 also can include a cap device 130 to retain the fluid cartridge 120 in the cavity 116 of the housing structure 110. The pump device 100 can include a drive system (described in more detail below) that advances a plunger 125 in the fluid cartridge 120 so as to dispense fluid therefrom. The controller device 200 communicates with the pump device 100 to control the operation of the drive system. When the controller device 200, the pump device 100 (including the cap device 130), and the fluid cartridge 120 are assembled together, the user can (in some embodiments) conveniently wear the infusion pump system 10 on the user's skin under clothing, in a pouch clipped at the waist (e.g., similar to a cell phone pouch), or in the user's pocket while receiving the fluid dispensed from the pump device 100.

In some embodiments, the controller device 200 may be configured as a reusable component that provides electronics and a user interface to control the operation of the pump device 100. In such circumstances, the pump device 100 can be a disposable component that is disposed of after a single use. For example, as described in more detail below in connection with FIGS. 4-5, the pump device 100 can be a "one time use" component that is thrown away after the fluid cartridge 120 therein is exhausted. Thereafter, the user can removably attach a new pump device 100' (having a new medicine cartridge 120') to the reusable controller device 200 for the dispensation of fluid from a new fluid cartridge 120'. Accordingly, the user is permitted to reuse the controller device 200 (which may include complex or valuable electronics, as well as a rechargeable battery) while disposing of the relatively low-cost pump device 100 after each use. Such a pump system 10 can provide enhanced user safety as a new pump device 100' (and drive system therein) is employed with each new fluid cartridge 120'.

Figure 6:
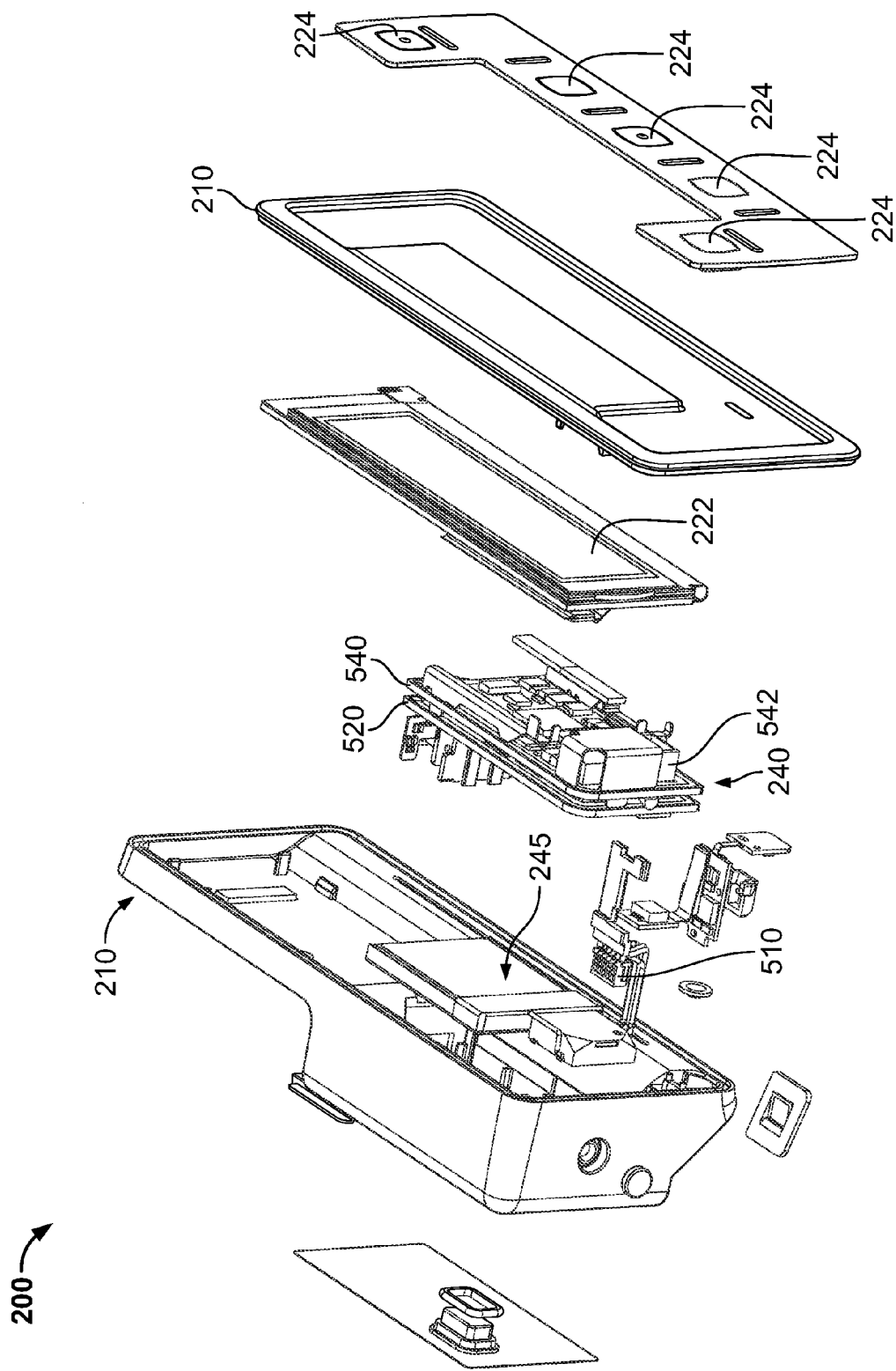
FIG. 6 is an exploded perspective view of a controller device for an infusion pump system, in accordance with some embodiments.

The infusion pump system 10 may also include a rechargeable battery pack 245 (also referred to herein as rechargeable battery 245; refer also to FIGS. 6-7) in the controller device 200 and a charger battery 345 (refer also to FIG. 8) in the pump device 100. The charger battery 345 can be disposable in that it can be discarded with the pump device 100 after exhaustion of the pump device 100. The rechargeable battery pack 245 can receive electrical energy from the charger battery 345 to maintain a battery of the rechargeable battery pack 245 at a charge greater than a threshold charge level. As described in more detail below, the rechargeable battery 245 can provide electrical energy to electronics of the controller device 200 and, in some circumstances, to the drive system 300 (FIG. 8) of the pump device 100 to dispense medicine to the patient. For example, if the charger battery 345 housed in the pump device becomes depleted, the rechargeable battery 245 housed in the controller device 200 can provide electrical power to the drive system of the pump device to continue the medicine dispensation dosages. Accordingly, infusion pump system 10 can incorporate two batteries 245 and 345 so that the rechargeable battery 245 housed in the controller device 200 is recharged by the second battery 345 housed in the pump device 100 when the controller device 200 is removably attached to the pump device 100. As described in more detail below, this feature also permits the rechargeable battery 245 to be stored (prior to use) in a "sleep" mode to conserve battery power and then switched to a normal mode by merely attaching the pump device 100 to the controller device 200. In other embodiments, a monolithic infusion pump system can include a rechargeable energy source 245 and a replaceable battery 345, which can be individually removed from the infusion pump system.

As described in more detail below in connection with FIGS. 6-10, the controller device 200 can include circuitry to minimize current drain of the rechargeable battery 245. Because current drain of the rechargeable battery reduces the amount of rechargeable battery energy available to power electronics of the infusion pump system 10, including electronics of the controller device 200 and the pump assembly 100, minimizing current drain of the rechargeable battery may be a priority. For example, it may be desirable to minimize current drain between the time that the rechargeable battery 245 is manufactured and the time it is first used. It may similarly be desirable to minimize current drain of the rechargeable battery 245 when the pump assembly 100 (including charger battery 345) is disconnected from the controller device 200, especially if the controller device remains disconnected from a new pump assembly and charger battery for an extended period of time, such as one or more days. The techniques described herein may permit the rechargeable battery 245 to be placed in a "low power" mode (such as a "sleep" or "storage" mode) even when the rechargeable battery 245 is at substantially full power level, which may minimize or otherwise reduce an amount of current drawn from the rechargeable battery 245 and thereby conserve remaining electrical charge of the rechargeable battery 245. Additionally, the techniques described herein may permit the rechargeable battery 245 to be placed in the low power mode without application of an external voltage source, and may be initiated based on an action of a user, or during a manufacturing or production step, according to various implementations.

Briefly, in use, the pump device 100 is configured to removably attach to the controller device 200 in a manner that provides a secure fitting, an overall compact size, and a reliable electrical connection that is resistant to water migration. For example, as described in more detail below in connection with FIGS. 1-5, the controller device 200 can include a housing 210 having a number of features that mate with complementary features of the pump housing 110. In such circumstances, the controller device 200 can removably attach with the pump device 100 in a generally side-by-side configuration. The compact size permits the infusion pump system 10 to be discrete and portable (as described below in connection with FIG. 3). Moreover, at least one of the pump device 100 or the controller device 200 can include a release member that facilitates an easy-to-use detachment and replacement process.

Referring again to FIG. 1, the pump system 10 can be a medical infusion pump system that is configured to controllably dispense a medicine from the cartridge 120. As such, the fluid cartridge 120 can contain a medicine 126 to be infused into the tissue or vasculature of a targeted individual, such as a human or animal patient. For example, the pump device 100 can be adapted to receive a medicine cartridge 120 in the form of a carpule that is preloaded with insulin or another medicine for use in the treatment of Diabetes (e.g., Byetta®, Symlin®, or others). Such a cartridge 120 may be supplied, for example, by Eli Lilly and Co. of Indianapolis, Ind. Other examples of medicines that can be contained in the fluid cartridge 120 include: pain relief drugs, hormone therapy, blood pressure treatments, anti-emetics, osteoporosis treatments, or other injectable medicines. The fluid cartridge 120 may have other configurations. For example, the fluid cartridge 120 may comprise a reservoir that is integral with the pump housing structure 110 (e.g., the fluid cartridge 120 can be defined by one or more walls of the pump housing structure 110 that surround a plunger to define a reservoir in which the medicine is injected or otherwise received).

In some embodiments, the pump device 100 can include one or more structures that interfere with the removal of the medicine cartridge 120 after the medicine cartridge 120 is inserted into the cavity 116. For example, the pump housing structure 110 can include one or more retainer wings that at least partially extend into the cavity 116 to engage a portion of the medicine cartridge 120 when the medicine cartridge 120 is installed therein. Such a configuration may facilitate the "one-time-use" feature of the pump device 100. In some embodiments, the retainer wings can interfere with attempts to remove the medicine cartridge 120 from the pump device 100, thus ensuring that the pump device 100 will be discarded along with the medicine cartridge 120 after the medicine cartridge 120 is emptied, expired, or otherwise exhausted. Accordingly, the pump device 100 can operate in a tamper-resistant and safe manner because the pump device 100 can be designed with a predetermined life expectancy (e.g., the "one-time-use" feature in which the pump device is discarded after the medicine cartridge 120 is emptied, expired, or otherwise exhausted).

Still referring to FIG. 1, the controller device 200 can be removably attached to the pump device 100 so that the two components are mechanically mounted to one another in a fixed relationship. Such a mechanical mounting can form an electrical connection between the removable controller device 200 and the pump device 100. For example, the controller device 200 can be in electrical communication with a portion of a drive system (not shown in FIG. 1) of the pump device 100. As described in more detail below, the pump device 100 can include a drive system that causes controlled dispensation of the medicine or other fluid from the cartridge 120. In some embodiments, the drive system incrementally advances a piston rod (not shown in FIG. 1) longitudinally into the cartridge 120 so that the fluid is forced out of an output end 122. A septum 121 (FIG. 1) at the output end 122 of the fluid cartridge 120 can be pierced to permit fluid outflow when the cap device 130 is connected to the pump housing structure 110. For example, the cap device may include a penetration needle that punctures the septum 121 during attachment of the cap device 130 to the housing structure 110. Thus, when the pump device 100 and the controller device 200 are attached and thereby electrically connected, the controller device 200 communicates electronic control signals via a hardwire-connection (e.g., electrical contacts or the like) to the drive system or other components of the pump device 100. In response to the electrical control signals from the controller device 200, the drive system of the pump device 100 causes medicine to incrementally dispense from the medicine cartridge 120. Power signals, such as signals from the rechargeable battery 245 of the controller device 200 and from the charger battery 345 of the pump device 100 may also be passed between the controller device 200 and the pump device 100.

As shown in FIG. 1, the pump device 100 can include an electrical connector 118 (e.g., having conductive pads, pins, and the like) that is exposed to the controller device 200 and that mates with a complementary electrical connector (refer to connector 218 in FIG. 2) on the adjacent face of the controller device 200. The electrical connectors 118 and 218 provide the electrical communication between the control circuitry (refer, for example, to FIGS. 6, 7A and 7B) housed in the controller device 200 and at least a portion of the drive system or other components of the pump device 100. For example, in some embodiments, the electrical connectors 118 and 218 can permit the transmission of electrical control signals to the pump device 100 and the reception of feedback signals (e.g., sensor signals) from particular components within the pump device 100. The electrical connectors 118 and 218 may similarly facilitate transmission of one or more power signals from the rechargeable battery pack 245 to the pump device 100, where the signals may be used to provide power to components of the pump device 100, or to transmit one or more power signals from the charger battery 345 to the controller device, where the signals may be used to charge the rechargeable battery 245 or to power components of the controller device 200.

Still referring to FIG. 1, the controller device 200 can include a user interface 220 that permits a user to monitor the operation of the pump device 100. In some embodiments, the user interface 220 can include a display device 222 and one or more user-selectable buttons (e.g., several buttons 224 are shown in the embodiment of FIG. 1). The display device 222 can include an active area in which numerals, text, symbols, images, or a combination thereof can be displayed. For example, the display device 222 can be used to communicate a number of settings or menu options for the infusion pump system 10. In this embodiment, the user may press one or more of the buttons to shuffle through a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining in the cartridge 120, or the like). In some embodiments, the user can adjust the settings or otherwise program the controller device 200 by pressing one or more buttons of the user interface 220. For example, in embodiments of the infusion pump system 10 configured to dispense insulin, the user may press one or more of the buttons to change the dispensation rate of insulin or to request that a bolus of insulin be dispensed immediately or at a scheduled, later time. In some implementations, the display device 222 may also be used to communicate information regarding remaining battery life.

Accordingly, when the controller device 200 is connected to the pump device 100, the user can be provided with the opportunity to readily monitor the infusion pump operation by simply viewing the user interface 220 of the controller device 200 connected to the pump device 100. Such monitoring capabilities may provide comfort to a user who may have urgent questions about the current operation of the pump device 100. Also, in these embodiments, there may be no need for the user to carry and operate a separate module to monitor the operation of the infusion pump device 100, thereby simplifying the monitoring process and reducing the number of devices that must be carried by the user. If a need arises in which the user desires to monitor the operation of the pump device 100 or to adjust the settings of the pump system 10 (e.g., to request a bolus amount of medicine), the user can readily operate the user interface 220 of the controller device 200, which is removably attached to the pump device 100, without the requirement of locating and operating a separate monitoring module.

Figure 2:
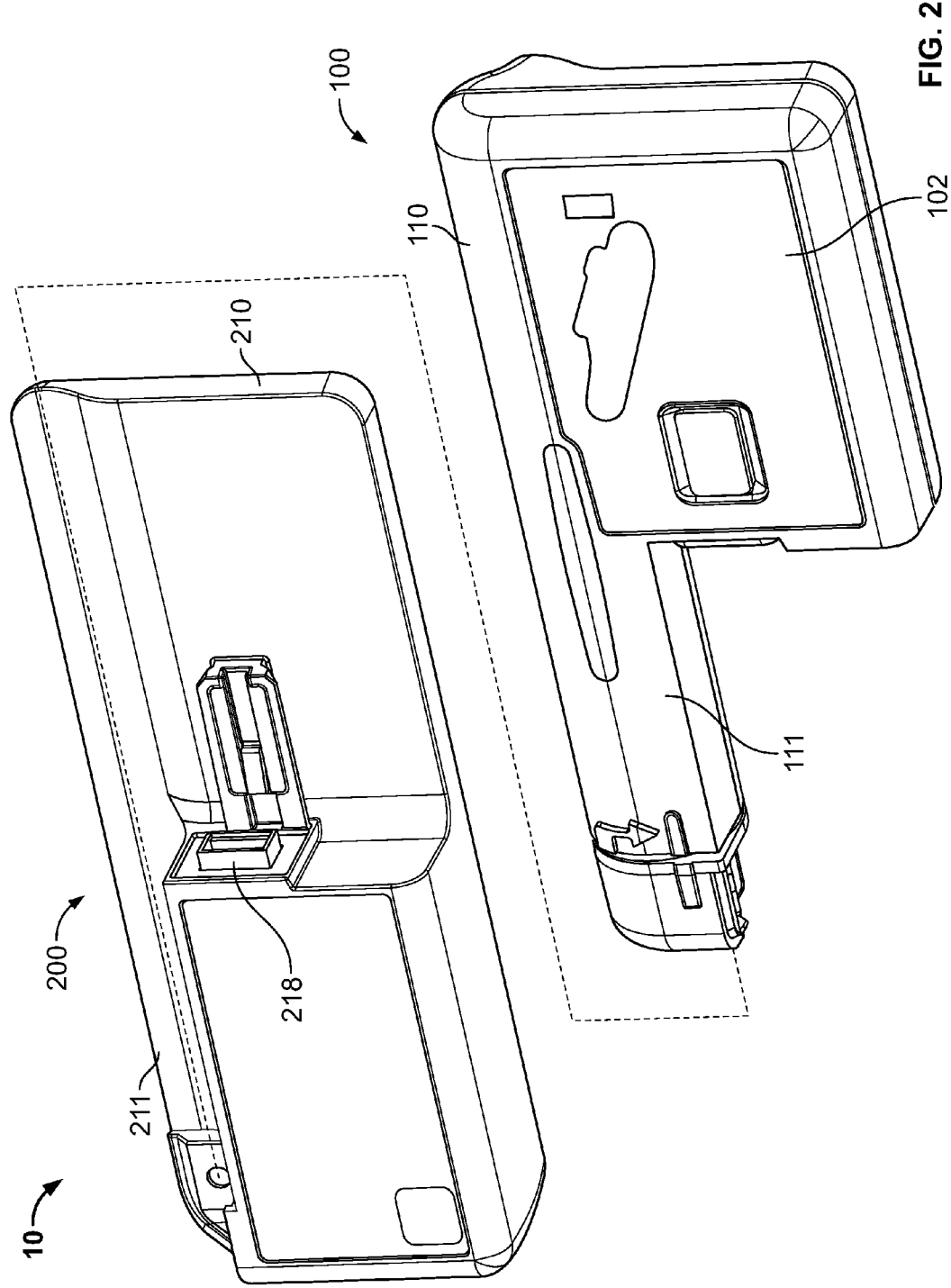
FIG. 2 is a perspective view of the infusion pump system of FIG. 1 in a detached state.

Referring now to FIG. 2, when the infusion pump system 10 operates, the controller device 200 can be removably attached to the pump device 100 in a side-by-side arrangement. For example, the pump device 100 may be moved in a longitudinal direction (e.g., refer to direction 219 in FIG. 4) toward the controller device 200 until the complementary features connect and secure the separate components in the side-by-side arrangement. In these circumstances, the pump device 100 and the controller device 200 can be separate components that fit together, but the overall size of the combined assembly can be reduced because there is no requirement for one component (e.g., the controller device or pump device) to surround or envelop the second component (e.g., the pump device or controller device). Moreover, in some embodiments, the pump device 100 and controller device 200 can be readily attached together with a "one-movement" process that is convenient to the user.

The controller device 200 can include a controller housing structure 210 having a number of features that are configured to mate with complementary features of the pump housing structure 110 so as to form a releasable mechanical connection. For example, the pump housing structure 110 can include a barrel 111 that mates with a complementary barrel channel 211 of the controller housing 210. In various implementations, the pump device 100 and the controller device 200 can be mounted to one another so that the assembled system 10 is resistant to water migration both into the pump housing structure 110 and the controller housing structure 210. Such a configuration can also provide water-resistant protection for the electrical connection between the pump device 100 and the controller device 200. Thus, the sensitive internal components in the controller device 200 and the pump device 100 can be reliably protected from water migration if the user encounters water (e.g., rain, incidental splashing, and the like) while using the pump system 10.

Figure 3:
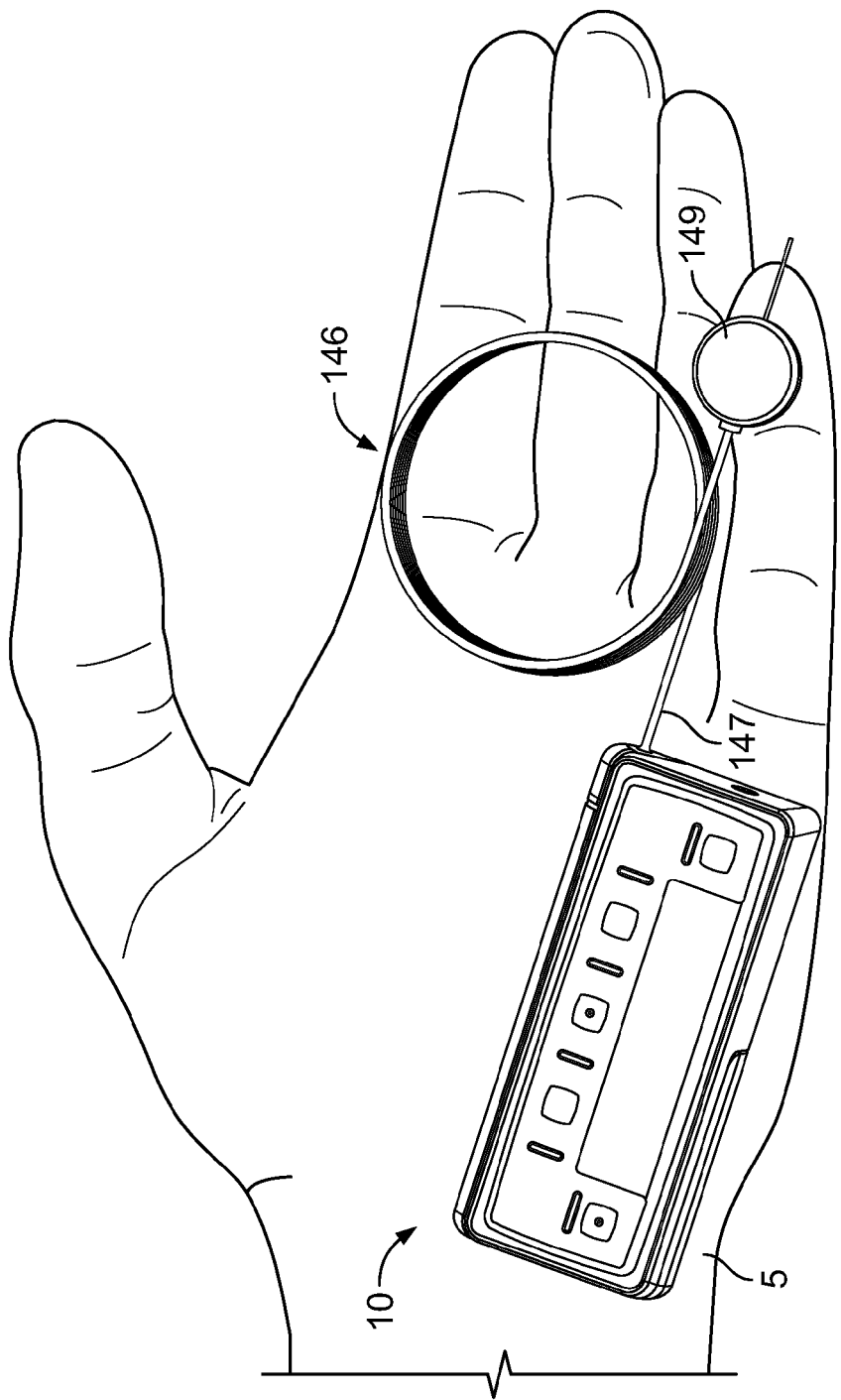
FIG. 3 is a perspective view of an infusion pump system, in accordance with some embodiments.

Referring to FIG. 3, the infusion pump system 10 can be configured to be portable and can be wearable and concealable. For example, a user can conveniently wear the infusion pump system 10 on the user's skin (e.g., skin adhesive) underneath the user's clothing or carry the pump device 100 in the user's pocket (or other portable location) while receiving the medicine dispensed from the pump device 100. The pump system 10 is shown in FIG. 3 as being held in a user's hand 5 so as to illustrate an exemplary size of the system 10 in accordance with some embodiments. This embodiment of the infusion pump system 10 is compact so that the user can wear the portable infusion pump system 10 (e.g., in the user's pocket, connected to a belt clip, adhered to the user's skin, or the like) without the need for carrying and operating a separate module. In such embodiments, the cap device 130 of the pump device 100 can be configured to mate with an infusion set 146. In general, the infusion set 146 can be a tubing system that connects the infusion pump system 10 to the tissue or vasculature of the user (e.g., to deliver medicine into the tissue or vasculature under the user's skin). The infusion set 146 can include a flexible tube 147 that extends from the pump device 100 to a subcutaneous cannula 149 that may be retained by a skin adhesive patch (not shown) that secures the subcutaneous cannula 149 to the infusion site. The skin adhesive patch can retain the infusion cannula 149 in fluid communication with the tissue or vasculature of the patient so that the medicine dispensed through the tube 147 passes through the cannula 149 and into the user's body. The cap device 130 can provide fluid communication between the output end 122 (FIG. 1) of the medicine cartridge 120 and the tube 147 of the infusion set 146.

In some embodiments, the infusion pump system 10 can be pocket-sized so that the pump device 100 and controller device 200 can be worn in the user's pocket or in another portion of the user's clothing. In some circumstances, the user may desire to wear the pump system 10 in a more discrete manner. Accordingly, the user can pass the tube 147 from the pocket, under the user's clothing, and to the infusion site where the adhesive patch can be positioned. As such, the pump system 10 can be used to deliver medicine to the tissues or vasculature of the user in a portable, concealable, and discrete manner.

In some embodiments, the infusion pump system 10 can be configured to adhere to the user's skin directly at the location in which the skin is penetrated for medicine infusion. For example, a rear surface 102 (FIG. 2) of the pump device 100 can include a skin adhesive patch so that the pump device 100 can be physically adhered to the skin of the user at a particular location. In these embodiments, the cap device 130 can have a configuration in which medicine passes directly from the cap device 130 into an infusion cannula 149 that is penetrated into the user's skin. In some examples, the user can temporarily detach the controller device 200 (while the pump device 100 remains adhered to the skin) so as to view and interact with the user interface 220.

Referring now to FIGS. 4-5, the infusion pump system 10 can be operated such that the pump device 100 is a disposable, non-reusable component while the controller device 200 is a reusable component. In these circumstances, the pump device 100 may be configured as a "one-time-use" device that is discarded after the medicine cartridge is emptied, expired, or otherwise exhausted. Thus, in some embodiments, the pump device 100 can be designed to have an expected operational life of about 1 day to about 30 days, about 1 day to about 20 days, about 1 to about 14 days, or about 1 day to about 7 days—depending on the volume of medicine in the cartridge 120, the dispensation patterns that are selected for the individual user, and other factors. For example, a medicine cartridge 120 containing insulin can have an expected usage life of about 7 days after the cartridge is removed from a refrigerated state and the septum 121 is punctured. In some circumstances, the dispensation pattern selected by the user can cause the insulin to be emptied from the medicine cartridge 120 before the 7-day period. If the insulin is not emptied from the medicine cartridge 120 after the 7-day period, the remaining insulin can become expired sometime thereafter. In either case, the pump device 100 and the medicine cartridge 120 therein can be discarded after exhaustion of the medicine cartridge 120 (e.g., after being emptied, expired, or otherwise not available for use).

The controller device 200, however, may be reused with subsequent new pump devices 100' and new medicine cartridges 120'. As such, the control circuitry, the user interface components, the rechargeable battery pack 245, and other components that may have relatively higher manufacturing costs can be reused over a longer period of time. For example, in some embodiments, the controller device 200 can be designed to have an expected operational life of about 1 year to about 7 years, about 2 years to about 6 years, or about 3 years to about 5 years—depending on a number of factors including the usage conditions for the individual user. Accordingly, the user can be permitted to reuse the controller device 200 (which can include complex or valuable electronics, and a rechargeable battery pack) while disposing of the relatively low-cost pump device 100 after each use. Such a pump system 10 can provide enhanced user safety as a new pump device 100' (and drive system therein) is employed with each new fluid cartridge 120'.

Referring to FIGS. 4-5, the same controller device 200 can be reused with a new pump device 100' having a new medicine cartridge 120' retained therein, and the previously used pump device 100, including the exhausted medicine cartridge, can be discarded in a discard bin 20. The new pump device 100' (FIG. 4) can have a similar appearance, form factor, and operation as the previously used pump device 100, and thus the new pump device 100' can be readily attached to the controller device 200 for controlled dispensation of medicine from the new medicine cartridge 120'. In some embodiments, the user can prepare the new pump device 100' for use with the controller device 200. For example, the user may insert the new medicine cartridge 120' in the cavity 116 of the new pump device 100' and then join the cap device 130 to the pump housing to retain the new medicine cartridge 120' therein (refer, for example, to FIG. 1). Although the tubing 147 of the infusion set 146 is not shown in FIG. 4, it should be understood that the tubing 147 can be attached to the cap device 130 prior to the cap device 130 being joined with the housing 110. For example, a new infusion set 146 can be connected to the cap device 130 so that the tubing 147 can be primed (e.g., a selected function of the pump device 100 controlled by the controller device 200) before attaching the infusion set patch to the user's skin. As shown in FIG. 4, the new medicine cartridge 120' may be filled with medicine such that the plunger 125 is not viewable through the barrel 111.

The new pump device 100' can be removably attached to the controller device 200 to assemble into the infusion pump system 10 for delivery of medicine to the user. As previously described, the guided motion in the longitudinal direction 219 provides the user with a convenient "one-movement" process to attach the pump device 100' and the controller device 200. For example, the user can readily slide the pump device 100' and the controller device 200 toward one another in a single movement (e.g., in the longitudinal direction 219) that causes both a physical connection and an electrical connection. Thus, the infusion pump system 10 can permit users to readily join the pump device 100' and the controller device 200 without compound or otherwise difficult hand movements—a feature that can be beneficial to child users or to elderly users.

Referring now to FIG. 6, the controller device 200 (shown in an exploded view) houses a number of components that can be reused with a series of successive pump devices 100. In particular, the controller device 200 can include controller circuitry 240 and rechargeable battery pack 245, each arranged in the controller housing 210. As described above, rechargeable battery pack 245 may provide electrical energy to components of controller circuitry 240, other components of the controller device (e.g., a display device 222 and other user interface components, sensors, or the like), or components of the pump device 100. Controller circuitry 240 may be configured to communicate control or power signals to the drive system of the pump device 100, or to receive power or feedback signals from the pump device 100.

In some embodiments, the controller circuitry 240 can include a logic board 520 in communication with a power board 540. In general, the logic board 520 (and also the power board 540) may include components that are used to control operation of the infusion pump system 10, and the power board 540 may include components that receive battery power signals from the rechargeable battery 245, the charger battery 345, or both, and provide sources of power for the electrical components of the controller device 200 and the pump device 100. It should be understood that although the logic board 520 are power board 540 are depicted as a printed circuit boards, one or both can have other forms, including multiple boards, a flexible circuit substrate, and other configurations. In some implementations, the logic board 520 and power board 540 may be combined as a single printed circuit board.

Still referring to FIG. 6, the user interface 220 of the controller device 200 can include input components and/or output components that are electrically connected to the controller circuitry 240. For example, the user interface 220 can include the display device 222 having an active area that outputs information to a user and buttons 224 that the user can use to provide input. Here, the display device 222 can be used to communicate a number of settings or menu options for the infusion pump system 10. In some embodiments, the controller circuitry 240 can receive input commands from a user's button selections and thereby cause the display device 222 to output a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining the cartridge 120, the amount of battery life remaining, or the like). As previously described, the controller circuitry 240 can be programmable to cause the controller circuitry 240 to change any one of a number of settings for the infusion pump system 10. For example, the user may provide one or more instructions to adjust a number of settings for the operation of the infusion pump system 10. Such settings may be stored in the memory devices arranged in the controller circuitry 240. The controller circuitry 240 can include other components, such as sensors, that are electrically connected to the logic board 520.

Some embodiments of the controller circuitry 240 can include a cable connector (e.g., a USB connection port or another data cable port) that is accessible on an external portion of the controller housing 210. As such, a cable can be connected to the controller circuitry 240 to upload data or program settings to the controller circuitry 240 or to download data from the controller circuitry 240. For example, historical data of medicine delivery can be downloaded from the controller circuitry 240 (via the cable connector) to a computer system of a physician or a user for purposes of analysis and program adjustments. Optionally, the data cable can also provide recharging power.

Figure 7A:
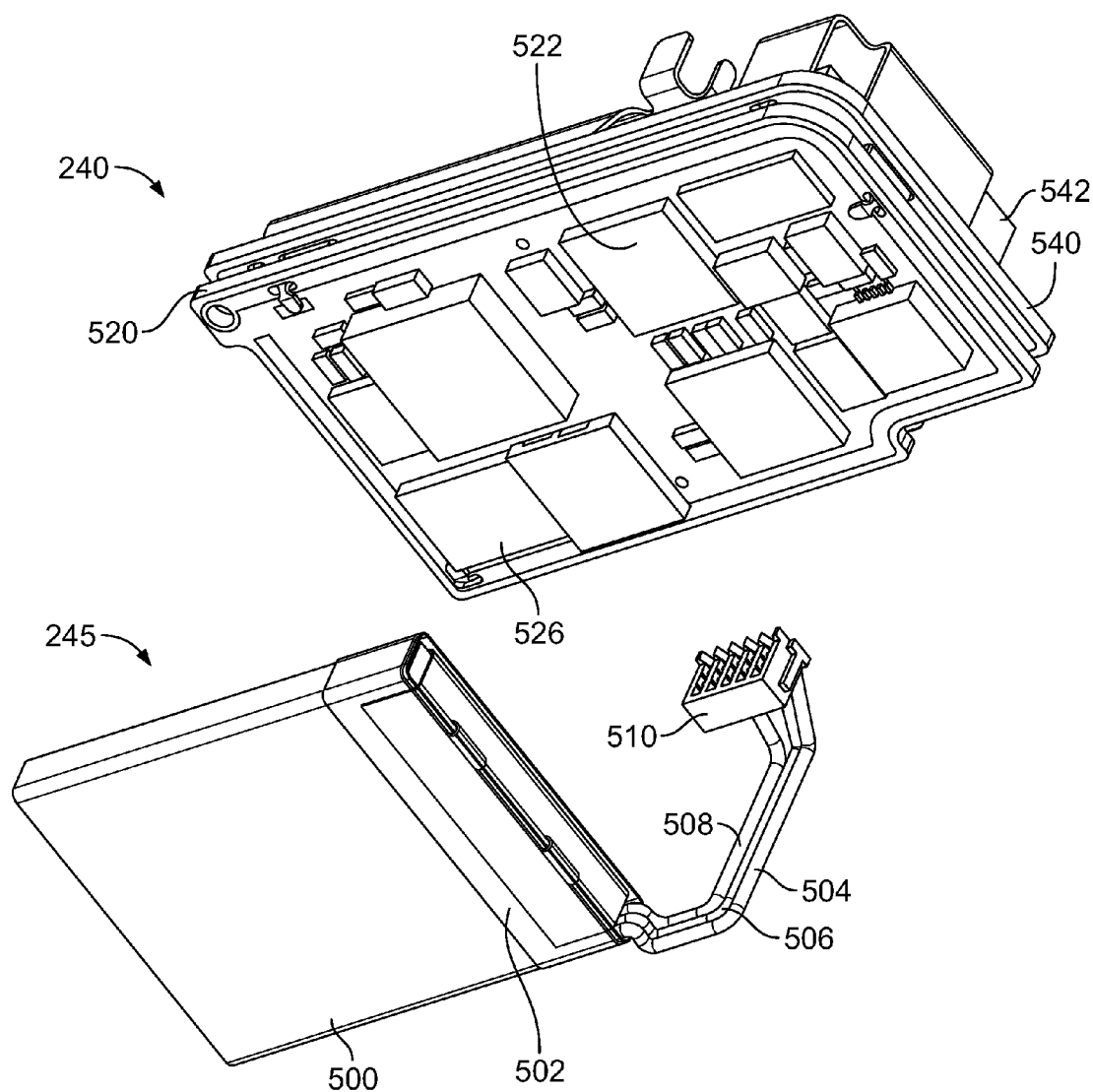

Referring now to FIG. 7A, a perspective view of portions of controller circuitry 240 and the rechargeable battery pack 245 is shown. Rechargeable battery pack 245 may include one or more lithium-ion or lithium-polymer battery cells 500, and may include a battery safety circuit 502 (described in more detail below in connection FIGS. 9-10). The rechargeable battery pack 245 includes three terminals 504, 506, and 508 according to some embodiments, as represented by wires 504, 506, and 508, which individually couple the terminals of the battery pack 245 to a connector 510. As will be described below with reference to FIGS. 9-10, the terminals may include a voltage output terminal 504 and a return terminal 506, as well as a third terminal 508 that can be used to place the rechargeable battery pack 245 into a low power mode (even when the it is substantially fully charged). Controller circuitry 240 includes logic board 520 and power board 540, and may include one or more pairs of mating connectors (not shown) that may permit signals to be coupled between the logic board 520 and the power board 540.

The rechargeable battery pack 245 can be coupled to the power board 540. For example, the connector 510 may be connected with a mating connector 542 disposed on the power board 540, and may thereby couple the three terminals 504, 506, 508 from the battery pack 245 to the power board 540 and further to one or more components for controller circuitry 240.

The rechargeable battery pack 245 can include a lithium-ion or lithium-polymer battery 500. In some implementations, the lithium-ion or lithium-polymer battery 500 may be a 3.8 volt battery. The rechargeable battery pack 245 can include a high-current-output battery that is capable of discharging a brief current burst to power, for example, the drive system 300 of the pump device 100, and can also provide energy sources for various electronic components of the infusion pump system 10. In other embodiments, it should be understood that the rechargeable battery 245 can include a capacitor device capable of being recharged over time and intermittently discharging a current burst to activate the drive system 300. Additional embodiments of the rechargeable battery 245 can include a combination of batteries and capacitors.

In some embodiments, one or more power supply components (e.g., disposed on power board 540) may receive charge energy from the rechargeable battery pack 245 and convert the energy into one or more usable power sources at one or more voltage levels for electronic components of the infusion pump system. The electronic components may reside, for example, in the pump assembly 100 or in the controller device 200.

The rechargeable battery 245 may be capable of accepting and storing electrical energy over time (e.g., "trickle charge"). For example, the rechargeable battery 245 can be charged with energy supplied from the charger battery 345, according to some implementations. The hard-wired transmission of electrical energy from the rechargeable battery 245 to the drive system 300 can occur through the previously described connectors 118 and 218 (FIGS. 1-2). The rechargeable battery 245 can receive electrical energy from a power source housed in the pump device 100 (e.g., the charger battery 345), from a plug-in wall charger, from a cable connector (e.g., a USB connection port that is connected to the controller circuitry 240), or from another charging device (e.g., a charging cradle), according to some implementations.

Accordingly, the infusion pump system 10 can include two power sources 345 and 245—one arranged in the disposable pump device 100 and another arranged in the reusable controller device 200—which can permit a user to continually operate the controller device 200 without having to recharge a battery via a plug-in wall charger or other cable. Because the controller device 200 can be reusable with a number of pump devices 100 (e.g., attach the new pump device 100' after the previous pump device 100 is expended and disposed), the rechargeable battery 245 in the controller device can be recharged over a period of time, each time when a new pump device 100' is connected thereto. Such a configuration can be advantageous in those embodiments where the pump device 100 is configured to be a disposable, one-time-use device that attaches to a reusable controller device 200. For example, in those embodiments, the "disposable" pump devices 100 recharges the rechargeable battery 245 in the "reusable" controller device 200, thereby reducing or possibly eliminating the need for separate recharging of the controller device 200 via a power cord plugged into a wall outlet.

Referring again to FIG. 7A, a main processor 522 is shown residing on logic board 520. In various implementations, processor 522 may comprise one or more microprocessors, microcontrollers, digital signal processors, instantiated cores within one or more programmable logic devices (e.g., application specific integrated circuit, field programmable gate array, complex programmable logic device), or the like. Processor 522 may execute instructions and perform tasks associated with the infusion pump system. For example, the processor 522 may coordinate the electrical communication to and/or from the controller device 200 (e.g., communication between the controller device 200 and the pump device 100). Processor 522 may receive inputs indicative of various statuses relating to the infusion pump system. For example, the processor 522 may receive one or more inputs that indicate a charge status of the rechargeable battery 245, a charge status of the charger battery 345, or both. As will be described in more detail below, the processor 522 may control a switch (e.g., switch 562 or switch 564, see FIGS. 9-10) that may cause the rechargeable battery pack 245 to enter a low power mode.

In various implementations, processor 522 executes instructions stored in memory locations internal of the processor 522 or in memory locations in one or more memory devices external of the processor 522. For example, in some embodiments the processor 522 may include on-board random access memory (RAM), where instructions may be loaded and executed therefrom by the processor 522. Processor 522 may also include various forms of on-board non-volatile memory for storing instructions or data in some implementations, including but not limited to EPROM, EEPROM, Flash, and the like. In some embodiments, memory devices external of the processor 522 are used. A memory device 526 may store instructions, data, or both, for use by the processor 522. In some implementations, memory device 526 includes FRAM data storage. Memory device 526 may store user settings and alarms, as well as parameters for the infusion pump system 10, including last-used pump parameters. As will be described below with reference to FIGS. 9-10, the processor 522 may provide an output that causes the rechargeable battery pack 245 to enter a low power mode.

Referring now to FIG. 7B, the controller circuitry 240 can include charger control circuitry, which can be disposed on the power board 540. The charger control circuitry can serve as a gatekeeper to operate the charging and discharging of the rechargeable battery 245. In some implementations, the charger control circuitry can cause the rechargeable battery 245 to output power to the electronics and display of the controller device 200, to output power to the drive system 300 housed in the pump device 100, to output power to one or more other components of the infusion pump system 10, to receive recharging power from the charger battery 345, or some combination of the foregoing. In some embodiments, the charger control circuitry can be activated so as to provide the recharging power to the rechargeable battery 245 from the charger battery 345. Optionally, a DC-DC converter can be used to boost the voltage input (e.g., 1.5V in some embodiments) from the charger battery 345 to a higher, charging output voltage, which may be used to charge the rechargeable battery 245. In some embodiments, the charging output voltage may be about 3.8 volts. In some embodiments, a series resistor may be used to limit a maximum battery charge current. Also, in some implementations, the charger control circuitry may cause the rechargeable battery 245 to be recharged when the pump body 100 is attached to the controller device 200.

Figure 8:
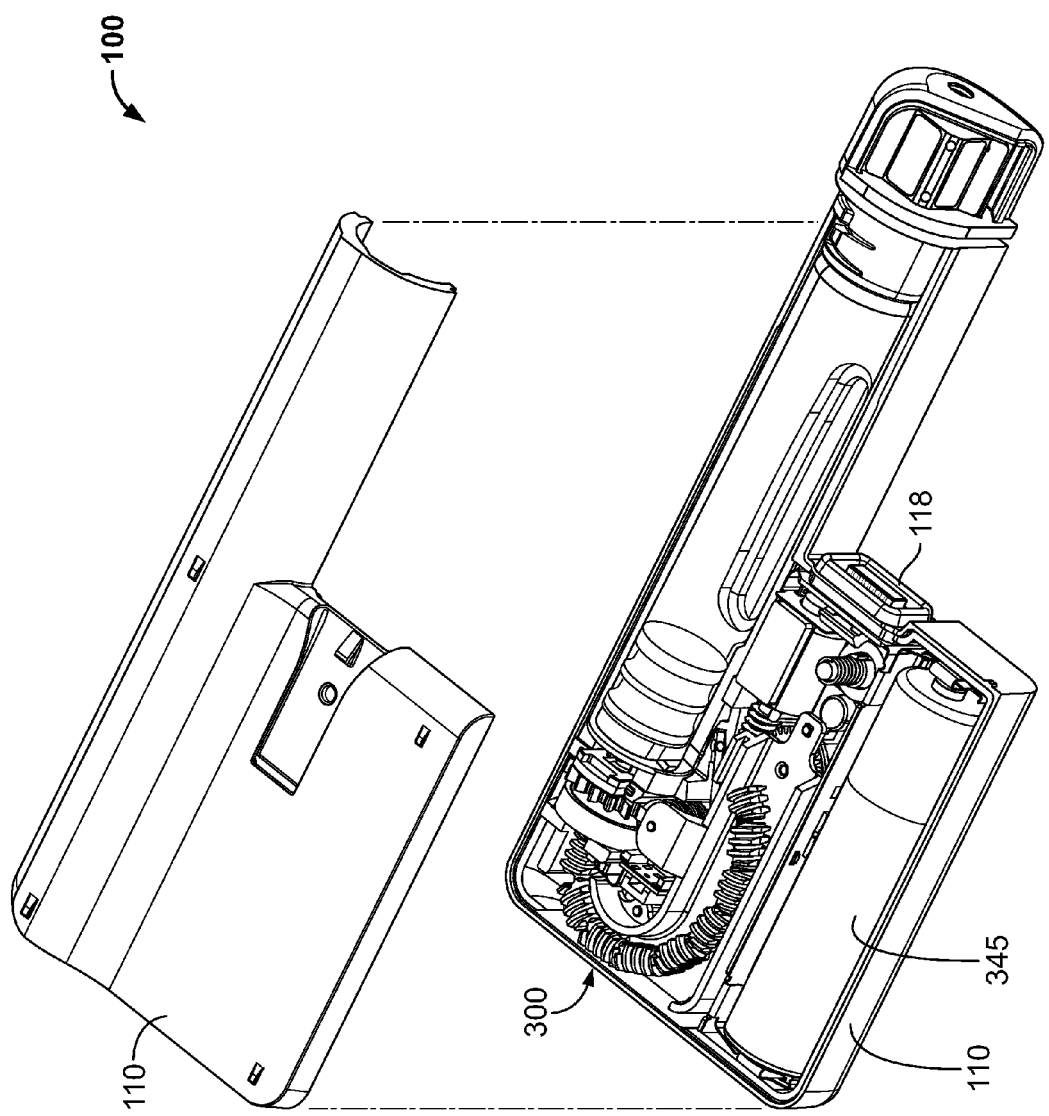
FIG. 8 is an exploded perspective view of a pump device for an infusion pump system, in accordance with some embodiments.

Referring now to FIG. 8, in some embodiments, the pump device 100 can include a power source 345, referred to above as a charger battery. In some embodiments, the power source 345 is an alkaline battery cell, such as a 1.5 Volt "AAA" alkaline battery cell. The power source 345 may be capable of transmitting electrical energy to the controller device 200 when the pump device 100 is attached to the controller device 200, via connectors 118 and 218 as described above. For example, the power source 345 may be used to charge the rechargeable battery pack 245 when the pump device 100 is attached to the controller device 200. In some embodiments, the power source 345 is used to provide energy to the drive system 300 of the pump device 100, and also to electronic components of the controller device 200. In some circumstances, the power source 345, which may be a "AAA" battery, may provide the energy to power all aspects of the infusion pump system 10. In some circumstances, the rechargeable battery 245 may provide the energy to power all aspects of the infusion pump system 10. In some circumstances, the rechargeable battery 245 and the power source 345 (charger battery) may each be responsible for powering particular aspects of the infusion pump system 10. In some circumstances, the rechargeable battery 245 may provide the energy to supplement the energy provided by the power source 345 to power aspects of the infusion pump system.

Referring again to FIG. 8, the pump device 100 can include the drive system 300 that is controlled by the controller device 200. The drive system 300 can accurately and incrementally dispense fluid from the pump device 100 in a controlled manner. The pump device 100 can include a connector circuit to facilitate the transfer of signals to and from the electrical connector 118. In some implementations, the connector circuit in the pump device 100 can include a memory device that can store data regarding the pump device 100 and its operational history. As previously described, the electrical connector 118 of the pump device 100 can mate with the connector 218 (FIG. 2) of the controller device 200 so that electrical communication can occur between the pump device 100 and the controller device 200. In some embodiments, the connector circuit can operate as a passageway for the control signals (from the controller circuitry 240 of the controller device 200) to transmit to the drive system 300. The connector circuit can also operate as a passageway for the electrical power from the charger battery 345 to pass to the controller device 200 for recharging of the rechargeable battery 245. Furthermore, the connector circuit can operate as a passageway for feedback signals from the drive system 300 to the controller circuitry 240 of the controller device 200.

Figure 9:
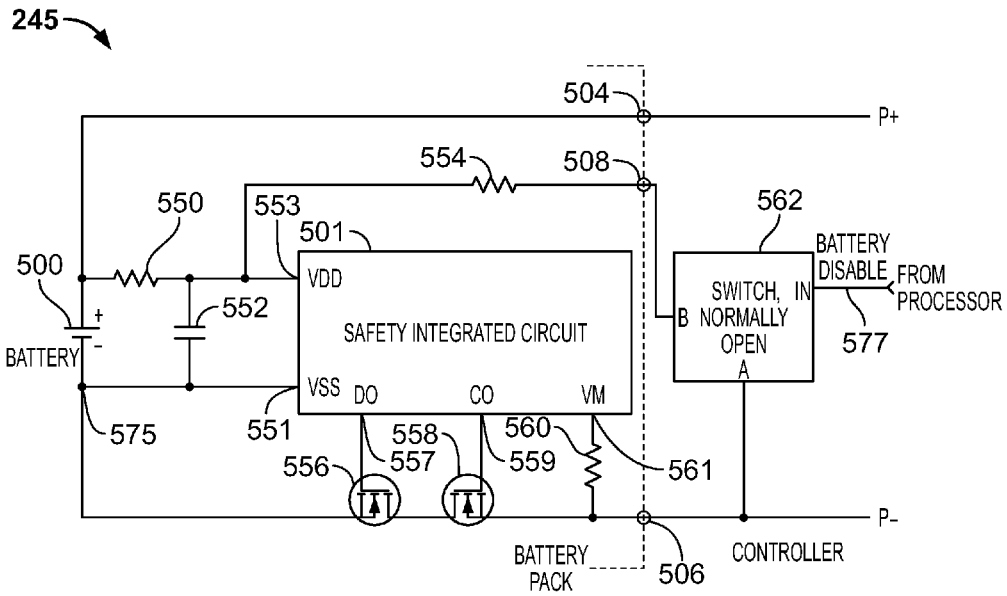
FIG. 9 is a schematic diagram of a battery pack device for an infusion pump controller, in accordance with some embodiments.

Referring now to FIG. 9, a schematic diagram of a battery pack device and circuit for an infusion pump controller is shown. The battery pack device may correspond to the rechargeable battery 245, according to some implementations. Using the techniques described herein, the battery pack device 245 may be placed into a low power mode, which may preserve a remaining charge of the battery pack and minimize idle current drain from the battery pack. A battery 500, such as the one or more rechargeable battery cells of battery pack 245, is coupled via a first resistor 550 to a voltage sense terminal 553 of a battery protection integrated circuit ("IC") 501. Additionally, the positive battery terminal is coupled to a voltage output terminal 504 of the battery pack 245. A capacitor 552 is coupled between the voltage sense terminal 553 and a ground reference 575 of the battery 500, to which a return terminal 551 of the battery protection IC 501 is also connected. The first resistor 550 and the capacitor 552 form a high-pass filter circuit to prevent battery voltage spikes from reaching the voltage input terminal 553 of the battery protection IC 501.

In some implementations, battery protection IC 501 may be a Seiko S-8211C device, although other battery protection devices may alternatively be used. In the embodiment shown in FIG. 9, three additional pins of the battery protection IC 501 are shown. Output pins "DO" 557 and "CO" 559 are coupled to switches 556 and 558, respectively, so that battery protection IC 501 may independently control the switches 556 and 558. One terminal of switch 556 is coupled to terminal of switch 558, while a second terminal of switch 556 is coupled to the ground reference 575 of the battery 500. A voltage monitoring terminal 561 of the battery protection IC 501 is coupled to a current limiting resistor 560, where the other terminal of the current limiting resistor 560 is connected to the second terminal of switch 558 and to a return terminal 506 of the battery pack 245. Switches 556 and 558 are depicted as MOSFETs, but other types of switches (e.g., bipolar junction transistors or the like) could alternatively be used.

Under normal operating conditions, the battery protection IC 501 controls switches 556 and 558 to be closed, so that a conductive path is formed (through switches 556, 558) between the ground reference 575 of battery 500 and the return terminal 506 of the battery pack 245. Also, under normal operating conditions the battery protection IC 501 monitors the voltage across its voltage sense terminal 553 and its return terminal 551, where this voltage is typically the voltage of battery 500. If the battery protection IC 501 detects that the voltage across its voltage sense terminal 553 and its return terminal 551 falls below a predetermined low voltage threshold value for a predetermined period of time, the battery protection IC 501 perceives an under-voltage condition and controls switch 556 to open, thereby breaking the conductive path between the ground reference 575 of the battery 500 and the return terminal 506 of the battery pack 245. In some embodiments, the low voltage threshold value may be about 2.8 volts. By contrast, if the battery protection IC 501 detects that the voltage across its voltage sense terminal 553 and its return terminal 551 is above a predetermined high voltage threshold value for a predetermined period of time, the battery protection IC 501 perceives an over-voltage condition and controls switch 558 to open, thereby also breaking the conductive path between the ground reference 575 of the battery 500 and the return terminal 506 of the battery pack 245.

In the case of a detected under-voltage condition, the battery protection IC 501 places the battery pack 245 in a low power mode. In the low power mode, the battery protection IC 501 may cease to monitor voltage across its voltage sense terminal 553 and its return terminal 551, which may reduce an amount of current drain from battery 500. For example, in low power mode, current consumption from the battery may be reduced to about 0.3 microamps in the case of a Seiko S8211C battery protection IC 501. This reduced current consumption may represent about 10% of the current required when the battery protection IC 501 is operating in normal mode, for example. Additionally and as described above, the battery protection IC 501 controls switch 556 to open while in low power mode. While operating in low power mode, the battery protection IC 501 monitors its "VM" pin 561, which as described above is coupled via current limiting resistor 560 to the return terminal 506 of the battery pack 245, and when a sufficiently high voltage is applied across the voltage output terminal 504 and the return terminal 506 of the battery pack 245, the battery protection IC 501 returns to normal mode and controls switch 556 to close. In this fashion, battery 500 may be recharged by the charge voltage applied at terminal pins 504 and 506.

The techniques discussed herein involve presenting, across the voltage sense terminal 553 and return terminal 551 of the battery protection IC 501, a voltage lower than the predetermined low voltage threshold value so that the battery protection IC 501 perceives an under-voltage condition and ceases to monitor the voltage of battery 500. By doing so, the energy supply of the battery 500 may be preserved in an efficient manner and over-discharge of the battery 500 may be prevented, which may prolong the useful life of the battery 500. This may be done, for example, even when a charge potential of the battery 500 (that is, the actual battery voltage) is greater than the predetermined low voltage threshold value.

For example, in some embodiments the battery 500 may be a 3.8 volt battery (when fully charged). As described above, the predetermined the low voltage threshold value for the battery protection IC 501 may be about 2.8 volts. As a first example, it may be desirable to cause the battery protection IC 501 to place the battery pack 245 in low power mode at the time the battery pack 245 is manufactured, or when the infusion pump system 10 is manufactured. In this example, even with a fully-charged or nearly fully-charged battery 500, the battery pack 245 may be caused to enter a low power mode using the techniques discussed herein, by causing a voltage of less than the low voltage threshold value (2.8 volts in this example) to be presented across the voltage sense terminal 553 and return terminal 551 of the battery protection IC 501. This may preserve the charge of the rechargeable battery during shipping and storage of the infusion pump system 10, so that the unit may be operational on receipt without first having to charge the rechargeable battery 245. As will be described further below, processor 522 may initiate the process by setting an output battery disable signal 577 low. When a new pump assembly 100' is attached to the controller device 200 and a charging voltage (e.g., 3.8 volts in some embodiments) is applied across the voltage output terminal 504 and return terminal 506 of the battery pack 245, the battery protection IC 501 may bring the battery pack 245 out of the low power mode.

As a second example, it may similarly be desirable to minimize current drain of the rechargeable battery 245 at times after the infusion pump system has been put into service, such as when the pump assembly 100 (including charger battery 345) is disconnected from the controller device 200, especially if the controller device remains disconnected from a new pump assembly and charger battery for an extended period of time, such as one or more days. In this example, the processor 522 may use the techniques disclosed herein to cause the battery protection IC 501 to place the battery pack 245 in a low power mode when the battery voltage reaches a second voltage threshold value, where the second voltage threshold value is higher than the predetermined low voltage threshold value of the battery protection IC 501. For example, when the battery voltage reaches a second voltage threshold value of about 3.1 volts, the processor 522 may set a battery disable output 577 low, which may cause the battery protection IC 501 to place the battery pack 245 in the low power mode, as will be described in more detail below. This may preserve the charge of the rechargeable battery until a new pump assembly 100' is attached to the controller device 200 and the rechargeable battery is recharged.

Referring again to FIG. 9, a switch 562, which may be an analog switch in some implementations, operates to couple pins "A" and "B" together (switch closed) while a logic low input is received on an input pin ("IN") of the switch. At all other times, the switch 562 is open, so that pins A and B of the switch are disconnected. Pin A of the switch 562 is coupled to the return terminal 506 of the battery pack 245, and to the ground reference 575 of battery 500 when switches 556 and 558 are closed, such as when battery protection IC 501 activates switches 556 and 558 (e.g., in normal mode). Pin B of the switch 562 is coupled to the third terminal 508 of the battery pack 245, and to one terminal of a second resistor 554. The other terminal of the second resistor 554 is coupled to the voltage sense terminal 553 of the battery protection IC 501.

In operation, when switch 562 receives a logic low input at its "IN" terminal, switch 562 internally switches to couple pins A and B together, thereby providing a low-resistance connection between the third terminal 508 of the battery pack 245 and the return terminal 506 of the battery pack 245. A battery disable signal 577 may be received by the switch 562 at the IN terminal of the switch 562. In some implementations, the processor 522 controls the battery disable signal 577, which is received by the switch 562. The battery disable signal 577 may be pulled high by a pull-up resistor (not shown) so that when the processor 522 is not driving the signal 577 low the switch 562 sees a logic high input and remains open (i.e., pins A and B not internally connected within the switch 562).

Still referring to FIG. 9, when switch 562 closes (e.g., as commanded by processor 522) and creates a low-resistance connection between the third terminal 508 of the battery pack 245 and the return terminal 506 of the battery pack 245, the first resistor 550 and the second resistor 554 create a resistive divider across the voltage sense terminal 553 of the battery protection IC 501. Values can be chosen for the first resistor 550 and the second resistor 554 so that the resistive divider formed by the resistors causes a voltage less than the predetermined low voltage threshold value of the battery protection IC 501 to be presented at the voltage sense terminal 553 of the battery protection IC 501 for expected values of the battery 500. For example, the first resistor 550 may have a value of 220 ohms, and the second resistor 554 may have a value of 540 ohms. In this case, even if battery 500 is fully charged at 3.8 volts, a voltage of 2.7 volts will be presented to the battery protection IC 501 when switch 562 closes and current flows through the first resistor 550 and the second resistor 554, and the battery protection IC 501 will place the battery pack 245 in low power mode because the sensed voltage (2.7 volts) is lower than the predetermined low voltage threshold value (2.8 volts).

Figure 10:
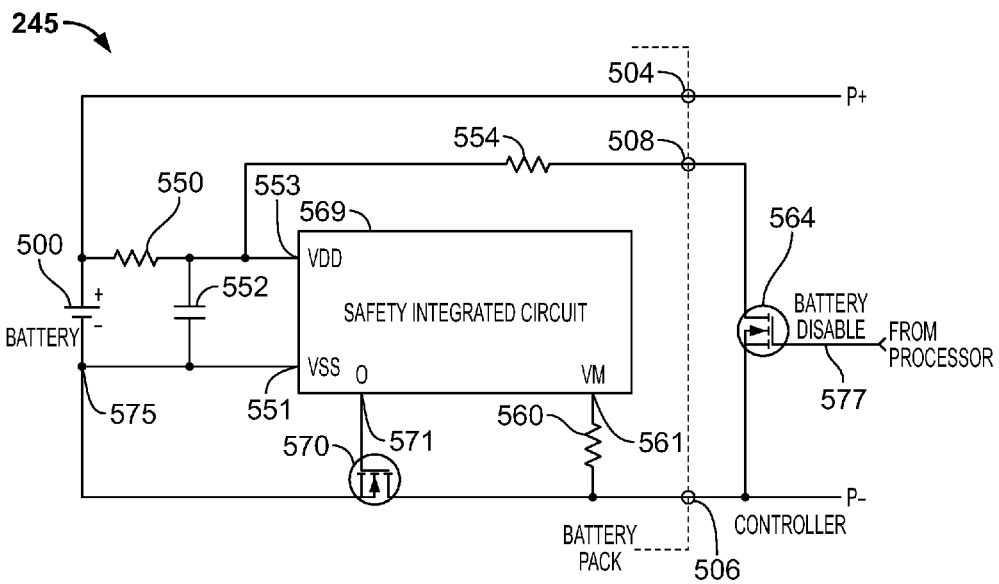
FIG. 10 is another schematic diagram of a battery pack device for an infusion pump controller, in accordance with some embodiments.

Referring now to FIG. 10, another schematic diagram of a battery pack device and circuit for an infusion pump controller is shown. The battery pack device may correspond to the rechargeable battery 245, according to some implementations. FIG. 10 differs from FIG. 9 in three respects. First, switch 564 is a MOSFET, in contrast to the analog switch 562 of FIG. 9, but operates in similar fashion, normally remaining open but being activated (closed) when the battery disable signal 577 goes low. When the switch 564 closes, a low-resistance connection is provided between the third terminal 508 of the battery pack 245 and the return terminal 506 of the batter pack 245, and a low power mode is entered as described above. Second, safety IC 569 is shown generically with a single output terminal "O" 571, where the safety IC 569 may activate the output terminal 571 when either an under-voltage or over-voltage condition is sensed. Alternatively, output terminal 571 may correspond to "DO" terminal 557 (FIG. 9) in some implementations. Third, a single switch 570 replaces switches 556 and 558 of FIG. 9.

It should be understood that, in some embodiments, the battery pack device 245 can be triggered to shift into or out of the low power without the use of a switch 562 or 564. For example, as an alternative to employing the switch 262 or 264 between the processor and the battery pack device, a pin of the processor 522 can be coupled directly to the third terminal 508 of the battery pack 245, thereby omitting the switch 562 (FIG. 9) or 564 (FIG. 10). In such circumstances, an output pin of processor 522 provides the battery disable signal 577 directly to the third terminal 508 of the battery pack 245, without using devices 562 or 564 as buffers. This embodiment may be used, for example, for a processor housed in the controller device 200 having an I/O pin rated to withstand a full-battery voltage (e.g., about 3.8V in some implementations) and rated to sink a current (e.g., about 5 mA in some implementations) that flows through the resistive divider formed by the first resistor 550 and the second resistor 554 when a (logic low) battery disable signal 577 is applied by the processor 522. Accordingly, the processor included in the controller device 200 can be coupled directly to the third terminal 508 of the battery pack device in a manner that eliminates the need for the switch 562 (FIG. 9) or 564 (FIG. 10).

A number of embodiments have been described. Nevertheless, it will be understood that various modifications may be made without departing from the spirit and scope of this disclosure. For example, other battery chemistries are also contemplated, particularly those where it is desirable to prevent excessive charging or discharging across a single cell of the battery, or across multiple cells of the battery. Also, it is contemplated that an existing signal terminal of a battery pack may be employed through use of a high-pass filter to separate the battery disable signal from lower frequency signals normally intended for the terminal, or by use of diode logic to separate positive-going from negative-going signals. Accordingly, other embodiments are within the scope of the following claims.

What is claimed is:

1. A portable infusion pump system, comprising:
   a pump device including: a pump housing that defines a space to receive a medicine, and a drive system to dispense the medicine from the pump device when the medicine is received in the space of the pump housing;
   a controller device electrically connectable to the pump device so as to control dispensation of medicine from the pump device, the controller device comprising:
      a battery pack including a voltage output terminal, a return terminal, a third terminal, and at least one rechargeable battery cell that is coupled to the voltage output terminal so as to provide electrical energy to at least one of a component of the controller device and the drive system of the pump device;
      a monitor circuit that is configured to sense a voltage of the at least one rechargeable battery cell;
      a first resistor coupled between the at least one rechargeable battery cell and a voltage sense terminal of the monitor circuit;
      a second resistor coupled between the voltage sense terminal of the monitor circuit and the third terminal of the battery pack;
      wherein when a low-resistance connection is provided between the third terminal of the battery pack and the return terminal of the battery pack, the monitor circuit is configured to shift the battery pack to a low power mode that reduces the electrical current drawn from the at least one rechargeable battery cell independent of the voltage of the at least one rechargeable battery cell.

2. The system of claim 1, further comprising a first switch coupled to a return terminal of the monitor circuit and to the return terminal of the battery pack, and controlled by the monitor circuit, wherein the monitor circuit causes the first switch to open when the monitor circuit puts the battery pack in the low power mode, thereby breaking an electrical connection between the return terminal of the monitor circuit and the return terminal of the battery pack.

3. The system of claim 1, wherein when a charging voltage is applied across the voltage output terminal of the battery pack and the return terminal of the battery pack, the monitor circuit shifts the battery pack to a normal mode in which a greater level of electrical current is drawn from the at least one rechargeable battery cell.

4. The system of claim 3, wherein the pump device further comprises a non-rechargeable battery, and wherein the charging voltage is derived from the non-rechargeable battery and applied across the voltage output terminal and the return terminal of the battery pack when the pump device and the controller device are removable attached to form an electrical connection.

5. The system of claim 1, wherein the controller device further comprises a processor and a second switch, the second switch coupled between the third terminal of the battery pack and the return terminal of the battery pack, and wherein the processor causes the second switch to close and provide the low-resistance connection between the third terminal of the battery pack and the return terminal of the battery pack.

6. The system of claim 5, wherein the second switch comprises a MOSFET.

7. The system of claim 1, wherein the low-resistance connection is provided between the third terminal of the battery pack and the return terminal of the battery pack without an external voltage source applied to any of the voltage output terminal, return terminal, or third terminal of the battery pack.

8. The system of claim 1, wherein, at a time when the low-resistance connection is provided between the third terminal of the battery pack and the return terminal of the battery pack, a potential of the at least one rechargeable battery cell is greater than a predetermined low voltage threshold value of the monitor circuit.

9. The system of claim 1, wherein the first resistor and the second resistor comprise a resistive divider across the voltage sense terminal of the monitor circuit when the low-resistance connection is provided between the third terminal of the battery pack and the return terminal of the battery pack.

10. The system of claim 1, wherein the low-resistance connection between the third terminal of the battery pack and the return terminal of the battery pack is provided in response to a user-initiated detachment of the pump device from the controller device.

11. The method of claim 1, wherein the low-resistance connection between the third terminal of the battery pack and the return terminal of the battery pack is provided in response to a user-initiated detachment of the pump device from the controller device.

12. A method of controlling a portable infusion pump system, comprising:
providing a controller device that is electrically connectable to a pump device so as to control dispensation of medicine from the pump device, the controller device comprising:
a battery pack including a voltage output terminal, a return terminal, a third terminal, and at least one rechargeable battery cell that is coupled to the voltage output terminal and that is configured to provide electrical energy to at least one of a user interface component of the controller device and a drive system of the pump device;
a monitor circuit that is configured to sense a voltage of the at least one rechargeable battery cell;
a first resistor coupled between the at least one rechargeable battery cell and a voltage sense terminal of the monitor circuit;
a second resistor coupled between the voltage sense terminal of the monitor circuit and the third terminal of the battery pack;
providing a low-resistance connection between the third terminal of the battery pack and the return terminal of the battery pack to cause the safety integrated circuit to put the battery pack in a low power mode that reduces electrical current drawn from the at least one rechargeable battery cell independent of the voltage of the at least one rechargeable battery cell; and
sending a control signal from the controller device to the pump device.

13. The method of claim 12, further comprising applying a charging voltage across the voltage output terminal of the battery pack and the return terminal of the battery pack causes the safety integrated circuit to reinstate the battery pack to a normal mode in which a greater level of electrical current is drawn from the at least one rechargeable battery cell.

14. The method of claim 13, wherein the pump device further comprises a non-rechargeable battery, and wherein the charging voltage is derived from the non-rechargeable battery and applied across the voltage output terminal and the return terminal of the battery pack when the pump device and the controller device are removably attached to form an electrical connection.

15. The method of claim 12, wherein the controller device further comprises a first switch coupled to a return terminal of the safety integrated circuit and to the return terminal of the battery pack, and controlled by the safety integrated circuit, and wherein the safety integrated circuit causes the first switch to open when the safety integrated circuit puts the battery pack in the low power mode, thereby breaking an electrical connection between the return terminal of the safety integrated circuit and the return terminal of the battery pack.

16. The method of claim 12, wherein the controller device further comprises a processor and a second switch, the second switch coupled between the third terminal of the battery pack and the return terminal of the battery pack, and wherein the processor causes the second switch to close and provide the low-resistance connection between the third terminal of the battery pack and the return terminal of the battery pack.

17. The method of claim 16, wherein the second switch comprises a MOSFET.

18. The method of claim 12, wherein providing the low-resistance connection between the third terminal of the battery pack and the return terminal of the battery pack to cause the safety integrated circuit to put the battery pack in a low power mode is implemented without applying an external voltage source to any of the voltage output terminal, return terminal, or third terminal of the battery pack.

19. The method of claim 12, wherein, at a time when the low-resistance connection is provided between the third terminal of the battery pack and the return terminal of the battery pack, a potential of the at least one rechargeable battery cell is greater than a predefined low voltage threshold value of the safety integrated circuit.

20. The method of claim 12, wherein the first resistor and the second resistor comprise a resistive divider across the voltage sense terminal of the safety integrated circuit when the low-resistance connection is provided between the third terminal of the battery pack and the return terminal of the battery pack.

* * * * *